(12) United States Patent
Arnold et al.

(10) Patent No.: US 7,220,563 B2
(45) Date of Patent: May 22, 2007

(54) GLUCOSE 6-OXIDASES

(75) Inventors: Frances H. Arnold, La Canada, CA (US); Lian-Hong Sun, El Cerrito, CA (US); Ioanna P. Petrounia, King of Prussia, PA (US)

(73) Assignee: California Institute of Technology, Pasadena, CA (US)

( * ) Notice: Subject to any disclaimer, the term of this patent is extended or adjusted under 35 U.S.C. 154(b) by 245 days.

(21) Appl. No.: 10/375,909

(22) Filed: Feb. 27, 2003

(65) Prior Publication Data

US 2003/0228673 A1    Dec. 11, 2003

Related U.S. Application Data

(60) Provisional application No. 60/400,417, filed on Aug. 1, 2002, provisional application No. 60/359,878, filed on Feb. 27, 2002.

(51) Int. Cl.
*C12N 9/02* (2006.01)
*C12N 1/20* (2006.01)
*C12N 15/00* (2006.01)
*C12Q 1/00* (2006.01)
*C12Q 1/68* (2006.01)
*C12P 21/04* (2006.01)
*C07H 21/04* (2006.01)

(52) U.S. Cl. ............. 435/189; 435/440; 435/69.1; 435/71.1; 435/4; 435/6; 435/252.3; 435/320.1; 435/23.2; 435/23.7

(58) Field of Classification Search ........... 435/189, 435/440, 4, 6, 252.3, 320.1, 69.1, 71.1; 536/23.2, 536/23.74, 23.7
See application file for complete search history.

(56) References Cited

U.S. PATENT DOCUMENTS

| | | | |
|---|---|---|---|
| 5,605,793 A | 2/1997 | Stemmer | 435/6 |
| 5,741,691 A | 4/1998 | Arnold et al. | 435/197 |
| 5,811,238 A | 9/1998 | Stemmer et al. | 435/6 |
| 5,830,721 A | 11/1998 | Stemmer et al. | 435/172.1 |
| 6,498,026 B2 | 12/2002 | Delagrave et al. | |

FOREIGN PATENT DOCUMENTS

| | | |
|---|---|---|
| WO | 95/22625 | 8/1995 |
| WO | 97/20078 | 6/1997 |
| WO | 98/42832 | 10/1998 |
| WO | 01/62938 | 8/2001 |
| WO | 01/88110 | 11/2001 |

OTHER PUBLICATIONS

Stratagene Catalog. 110-111. 2000-2001.*

(Continued)

*Primary Examiner*—P. Achutamurthy
*Assistant Examiner*—Yong D. Pak
(74) *Attorney, Agent, or Firm*—DLA Piper US LLP

(57) ABSTRACT

Glucose oxidase enzymes are provided, including novel variants of galactose oxidase enzymes. The polynucleotides that encode these novel variants can be expressed in recombinant host cell expression systems. The novel variant oxidase enzymes are capable of oxidizing compounds towards which wild-type galactose oxidase (e.g. D-galactose: oxygen 6-oxidoreductase, GAO; EC 1.1.3.9) has little or no activity. Preferred galactose oxidase variants are those which that have improved capability to oxidize secondary alcohols and/or D-glucose relative to the wild-type enzyme.

8 Claims, 9 Drawing Sheets

D-galactose

Galactose oxidase
GAO
→
$O_2$

D-galactohexodialdose

+ $H_2O_2$

OTHER PUBLICATIONS

NCBI—IGOF. 1998.*
Sequence Alignment—SEQ ID No. 2.*
Wikipedia—Glucose.*
Adanyi et al., European Food Research and Technology, 1999; 209:220-226.
Aisaka et al., Agric. Biol. Chem., 1981; 45(10):2311-2316.
Amaral et al., Methods Enzymol, 1966; 9:87-92.
Amaral et al., J. Biol. Chem., 1963; 238(7):2281-2284.
Arkin et al., Proc. Natl. Acad. Sci. USA, 1992; 89:7811-7815.
Arnold, F. H., Accounts Chem. Res., 1998; 31:125-131.
Arts et al., Synthesis, 1997, pp. 597-613.
Avigad, G., Arch. Biochem. Biophys., 1985; 239(2):531-537.
Avigad, G., Anal. Biochem., 1978; 86:470-476.
Avigad, G., J. Biol. Chem., 1962; 237(9):2736-2743.
Baron et al., J. Biol. Chem., 1994; 269(40):25095-25105.
Beckman et al., Biochemistry, 1985; 24:5810-5817.
Better et al., Science, 1988; 240:1041-1043.
Borman et al., J. Biol. Inorg. Chem., 1997; 2:480-487.
Cadwell et al., PCR Methods Applic., 1992; 2:28-33.
Calderhead et al., J. Biol. Chem., 1988; 263(25):12171-12174.
Carbon et al., In: Recombinant Molecules: Impact on Science and Society; edited by R.F. Beers, Jr. and E.G. Bassett, Raven Press: New York, 1977; ch. 33, pp. 355-378.
Castelli et al., Gene, 1994; 142:113-117.
Chen et al., Proc. Natl. Acad. Sci. USA , 1993; 90:5618-5622.
Cherry et al., Nat. Biotechnol., 1999;17:379-384.
Cooper et al., J. Biol. Chem., 1959; 234(3):445-448.
Crameri et al., Nature Biotechnol., 1996; 14:315-319.
Dahlhoff et al., Angew. Chem. Int. Ed. Engl, 1980; 19(7):546-547.
De Sutter et al., Gene, 1994; 141:163-170.
Delagrave et al., Bio/Technology, 1993; 11:1548-1552.
Delagrave et al., Protein Engineering, 1993; 6:327-331.
Dunford, H.B.,Peroxidases in Chemistry and Biology, 1991; 2:1-24.
Egorov et al., Ann. N.Y. Acad. Sci., 1991; 646:35-40.
Fiedler et al., Cell, 1995; 81:309-312.
Fitzgerald et al., Biochemistry, 1994; 33:3807-3818.
Gahmberg et al., Methods Enzymol., 1994; 230:32-44.
Gajhedé et al., Nature Struct. Biol., 1997; 4:1032-1038.
Gazaryan, I.G., LABPV Newsletters, 1994; 4:8-15.
Gietz et al., Yeast, 1995; 11:355-360.
Gillam et al., Arch. Biochem. Biophys., 1995; 319(2):540-550.
Giver et al., Proc. Natl. Acad. Sci. USA, 1998; 95:12809-12813.
Goldman et al., Bio/Technology, 1992; 10:1557-1561.
Goodin et al., Biochemistry, 1991; 30:4953-4962.
Goshorn et al., Cancer Res., 1993; 53:2123-2127.
Gram et al., Proc. Natl. Acad. Sci. USA, 1992; 89:3576-3580.
Guengerich et al., Meth. Enzymol., 1996; 272:35-44.
Gussow et al., Nucleic Acids Res., 1989; 17(10):4000-4000.
Hamilton et al., J. Am. Chem. Soc., 1978; 100(6):1899-1912.
Hamilton et al., In: Oxidases and Related Redox Systems, University Park Press, Baltimore, MD, 1973; 1:103-124.
Helenius, A., Mol. Biol. Cell., 1994; 5:253-265.
Hermes et al., Proc. Natl. Acad. Sci. USA, 1990; 87:696-700.
Hopps, H.B., Aldrichimica Acta, 2000; 33(1):28-30.
Horwitz et al., Proc. Natl. Acad. Sci. USA, 1986; 83:7406-7409.
Ishiguro et al., Carbohydr. Res., 2001; 331:423-430.
Ito et al., Methods Enzymol., 1995; 258:235-262.
Ito et al., J. Mol. Biol., 1994; 238:794-814.
Ito et al., Nature, 1991; 350:87-90.
Joo et al., Chem. Biol., 1999; 6(10):699-706.
Joo et al., Nature, 1999; 399:670-673.
Khosla et al., Bio/Technology, 8:849-853.
Kiba et al., J. Chromatogr., 1989; 463:183-187.
Klibanov et al., Biochem. Biophys. Res. Commun., 1982; 108(2):804-808.
Koroleva et al., Prikl. Biokhim. Mikrobiol., 1983; 19(5):632-637.
Kosman, D.J., In: Copper Proteins and Copper Enzymes, Rene Lontie, S.Sc., ed., CRC Press, Boca Raton, FL, 1984; vol. 2, Chapter 1, pp. 1-26.
Koster et al., Synthesis, 1982; 650-652.
Kyte J., In: Structure in Protein Chemistry, Garland Publishing Inc., New York & London, 1995, Chapter 7, pp. 243-279.
Lei, S. P.; Lin, H. C.; Wang, S. S.; Callaway, J.; Wilcox, G. J. Bacteriol. 169, 4379 (1987).
Leung, D. W. et al. (1989), Technique 1, 11-15.
Lis, M., and Kuramitsu, H.K. (1997), Antimicrob. Agents Chemother., 41(5), 999-1003.
Liu, X. C., and Dordick, J. S. (1999) J. Am. Chem. Soc. 121, 466-467.
Mannino et al., Italian Journal of Food Science, 1999; 11:57-65.
Maradufu, A., et al. Carbohydr. Res., 1974; 32:127-136.
Maradufu, A., et al. Carbohydr. Res., 1974; 32:93-99.
Maradufu, A., et al. Canad. J. Chem., 1971; 49:3429-3436.
Marrs, B. L. in IBC's Fifth Annual World Congress on Enzyme Technologies (2000) Las Vegas, NV.
Martin et al., Biomaterials, 1998; 19(1-3):69-76.
Martin et al., Food Chemistry, 1998; 61(3):281-286.
Mazur et al., J. Org. Chem., 1997; 62:4471-4475.
Mazur, A., In: Enzymes in Carbohydrate Synthesis, Bednarski, M. D. and Simon, E. S. Eds, 1991; Chapter 8, pp. 99-110.
McPherson et al., Biochem. Soc. Transact., 1993; 21:752-756.
McPherson et al., J. Biol. Chem., 1992; 267(12):8146-8152.
Mendonca et al., Arch. Biochem. Biophys., 1988; 266(2):427-434.
Mendonca et al., Arch. Biochem. Biophys., 1987; 252(2):507-514.
Miele et al., J.Biol.Chem., 1999; 274(12):7769-7776.
Miyazaki et al., J.Mol.Biol., 2000; 297:1015-1026.
Miyazaki et al., J. Mol. Evol., 1999; 49:716-720.
Moore et al., Nature Biotechnol., 1996; 14:458-.
Nagayama et al., J. Biol. Chem., 1998; 273(50):33423-33428.
Oliphant et al., Gene, 1986; 44:177-183.
Ortlepp et al., J. Biotechnol., 1989; 11:353-364.
Ostermeier et al., J. Biol. Chem., 1996; 271:10616-10622.
Rathore et al., FEBS Lett. 1996; 392:259-262.
Reynolds et al., J. Biol. Inorg. Chem., 1997; 2:327-335.
Rodriguez-Lopez et al., J.Biol.Chem., 1996; 271(8):4023-4030.
Romanos et al., Yeast, 1992; 8(6):423-488.
Root et al., J. Am. Chem. Soc., 1985; 107:2997-2999.
Said et al., Histol. Histopathol., 1999; 14:351-357.
Savenkova et al., Biochemistry, 1998; 37:10828-10836.
Saysell et al., JBIC, 1997; 2:702-709.
Schatz et al., Annu. Rev. Genet., 1990; 24:215-248.
Schlegel et al., Carbohydr. Res., 1968; 7:193-199.
Shafikhani et al., Biotechniques, 1997; 23:304-310.
Singh et al., J. Org. Chem., 1989; 54:2300-2307.
Sirotkin, K., J. Theor. Biol., 1986; 123:261-279.
Smith et al., Curr.Opin.Chem.Biol., 1998; 2:269-278.
Smith et al., J. Biol. Chem., 1990; 265(22):13335-13343.
Stemmer, W. P. C., Proc. Natl. Acad. Sci. USA, 1994; 91:10747-51.
Stemmer et al., Biotechniques, 1992; 14(2):256-265.
Studier et al., Meth. Enzymol., 1990; 185:60-89.
Sun et al., Protein Eng., 2001; 14:699-704.
Szabo et al.; Biosensors & Bioelectronics, 1996; 11(10):1051-1058.
Tams et al., FEBS Lett., 1998; 421:234-236.
Tkac et al., Biotechnology Techniques, 1999; 13:931-936.
Tressel et al., Methods Enzymol., 1982; 89:163-171.
Tressel et al., Anal. Biochem., 1980; 105(1):150-153.
Tressel, P. (1980) Ph.D. Thesis, State of University of New York, Buffalo.
Vega et al., Anal. Chim. Acta, 1998; 373:57-62.
Wachter et al., J. Am. Chem. Soc., 1996; 118:2782-2789.
Welinder, K. G., Eur J. Biochem, 1979; 96:483-502.
Whittaker et al., Biochemistry, 1998; 37:8426-8436.
Whittaker et al., J. Biol. Chem., 1988; 263(13):6074-6080.
Yang et al., Histol. Histopathol., 1996; 11:801-806.
Yano et al., Proc. Natl. Acad. Sci. USA , 1998; 95:5511-5515.
Zhao et al., Protein Eng., 1999; 12(1):47-53.
Zhao et al., Nucleic Acids Res., 1997; 25(6):1307-1308.

* cited by examiner ium NRRL 2903, formerly known as *Dactylium dendroides*, has been

GLUCOSE 6-OXIDASES

This application claims priority under 35 U.S.C. §119(e) to U.S. provisional patent applications No. 60/359,878, filed Feb. 27, 2002, and No. 60/400,417, filed Aug. 1, 2002, each of which is hereby incorporated by reference in its entirety.

FIELD OF THE INVENTION

This invention is concerned with oxidase enzymes with modified specificity and enzyme activity. The invention is particularly concerned with variant oxidase enzymes having activity towards compounds that are not encompassed by the substrate range of the corresponding wild-type enzyme.

BACKGROUND OF THE INVENTION

Enzyme catalysts have a myriad of existing and potential applications. Various techniques for creating new and improved enzyme variants are now available, allowing for the creation of large libraries of mutants or variants that can be screened for desired properties. For example, directed evolution has been successfully applied to improve a variety of enzyme properties, including substrate specificity, activity in organic solvents, and stability at high temperatures, which are often critical for industrial applications (Arnold, F. H. Accounts Chem. Res. 31, 125 (1998)). The directed evolution approach uses DNA shuffling for simultaneous random mutagenesis and recombination to generate a variant having an improved desirable property over the existing wild-type protein. Point mutations can be generated, for example, using the intrinsic infidelity of Taq-based polymerase chain reactions (PCR) associated with reassembly of nucleic acid sequences. In one example, Stemmer and coworkers applied this technique to the gene encoding for green fluorescence protein (GFP), which resulted in a protein that folded better than the wild type in *E. coli* (Crameri, A.; et al. Nature Biotechnol. 14, 315 (1996)). However, the need for new enzymes having new or enhanced biological properties remains. For example, to date, there are no known enzymes that selectively oxidize the 6-hydroxyl group of D-glucose. Such enzymes would be useful, particularly for chemical synthesis applications.

Galactose oxidase (D-galactose: oxygen 6-oxidoreductase, GAO), designated EC 1.1.3.9 by the Nomenclature Committee of the International Union of Biochemistry and Molecular Biology, is an oxidation enzyme containing a single copper ion. GAO is secreted by a number of fungal species, but no bacterium has been reported to produce the enzyme (Aisaka, K., and Terada, O., (1981), Agric. Biol. Chem., 45(10), 2311–2316).

GAO from one particular fungal species, *Fusarium* NRRL 2903, formerly known as *Dactylium dendroides*, has been extensively studied (Borman, C. D. et al. (1997) J. Biol. Inorg. Chem. 2,480–487). *Fusarium* GAO is a glycoprotein with a carbohydrate content of about 1.7% and consists of a single polypeptide chain of 639 amino acid residues with a molecular mass of 68 kD (the cDNA sequence is depicted in SEQ ID NO:1, which corresponds to nucleotide residues 962 to 2878 of GenBank Accession No. M86819; and the amino acid sequence in SEQ ID NO: 2, which corresponds to amino acid residues 42 to 680 of GenBank accession No. AAA16228.1 (Mendonca, M. H., and Zancan, G. T. (1987) Arch. Biochem. Biophys. 272, 507–514; Ito, N., et al. (1994) J. Mol. Biol. 238, 794–81477).

The reaction catalyzed by galactose oxidase (GAO) is the oxidation of primary alcohols to the corresponding aldehydes, coupled to the two-electron reduction of $O_2$ to hydrogen peroxide (Whitaker, M. W., and Whitaker, J. W. (1988) J. Biol. Chem. 263, 6074–6080). See FIG. 1. Galactose oxidase (GAO) is capable of oxidizing the hydroxyl group of the sixth carbon of D-galactose. The kinetic parameters of GAO for the oxidation of galactose are: $K_m$=67 mM, $k_{cat}$=3,000 $sec^{-1}$, $k_{cat}/K_m$=45×$10^3$ $M^{-1}sec^{-1}$ (Baron, A. J. (1994) J. Biol. Chem. 269, 25095–25105). GAO exhibits prochiral specificity (only the pro-S hydrogen is abstracted) as well as enantiomeric specificity for galactose (only D-galactose is oxidized by the enzyme) (Avigad, G., et al. (1962) J. Biol. Chem. 237, 2736–2743, Maradufu, A., et al. (1971) Canad. J. Chem. 49, 3429–3436).

In addition to D-galactose, GAO oxidizes a broad range of substrates. For example, GAO also accepts alpha- and beta-galactopyranosides, oligo- and polysaccharides and considerably smaller molecules, such as glycerol and allyl alcohol, as well as many other kinds of sugars and primary alcohols. However, in spite of the broad substrate specificity of GAO, it discriminates against D-glucose, the C-4 epimer of D-galactose, as a substrate or ligand. D-glucose does not bind to GAO, even at concentrations as high as 1M (Avigad, G., et al. (1962) J. Biol. Chem. 237, 2736–2743; Wachter, R. M., and Branchaud, B. L. (1996) J. Am. Chem. Soc. 118, 2782–2789).

GAO has one copper (II) ion associated with its active site and related to its oxidation properties. The GAO enzyme has three predominantly beta-structure domains (Ito, N., et al. (1991) Nature 350, 87–90). The copper ion lies on the solvent-accessible surface of the second and largest domain (residues 156–532) (Ito, N., et al. (1994) J. Mol. Biol. 238, 794–814; Ito, N., et al. (1995) Methods Enzymol. 258, 235–262). Tyr-272, Tyr-495, His-496, His-581 and a water molecule are the copper ligands at pH 7.0. The crystal structure also reveals a novel thioether bond linking Cys-228 and Tyr-272 and supports the presence of a tyrosine free radical at the active site (Whitaker, M. W., and Whitaker, J. W. (1988) J. Biol. Chem. 263, 6074–6080). A 3-D model of GAO and its active site structure is shown in FIG. 2.

Structure and amino acid residues related to GAO catalysis have been characterized and reported (Borman, C. D., et al. (1997) J. Biol. Inorg. Chem. 2, 480–487; Ito, N., et al. (1994) J. Mol. Biol. 238, 794–814; Wachter, R. M., and Branchaud, B. L. (1996) J. Am. Chem. Soc. 118, 2782–2789; Baron, A. J., et al. (1994) J. Biol. Chem. 269, 25095–25105; Ito, N., et al. (1991) Nature 350, 87–90; Reynolds, M. P., et al. (1997) J. Biol. Inorg. Chem. 2, 327–335; McPherson, M. J., et al. (1993), Biochem. Soc. Transact., 21, 752–756. (See also FIG. 2). For example, site-directed mutagenesis of Tyr-495 and Cys-228 have confirmed their involvement in galactose oxidation (Baron, A. J., et al. (1994) J. Biol. Chem. 269, 25095–25105; Reynolds, M. P., et al. (1997) J. Biol. Inorg. Chem. 2, 327–335). In addition, models illustrating residues involved in galactose binding have been proposed. For example, tryptophan 290 (W290) has been identified as a component of the free radical site of galactose oxidase (Baron, A. J., et al. (1994) J. Biol. Chem. 269, 25095–25105). The crystal structure also demonstrated that four residues, (histidine 496 and 581 (H496 and H581) and tyrosine 272 and 495 (Y272 and Y495) coordinate the cooper ion of galactose oxidase (Ito, N., et al. (1994) J. Mol. Biol. 238, 794–814). A pocket containing phenylalanines 194 and 464 (F194 and F464) interacts with the D-galactose backbone. See FIG. 2. These models may explain why galactose oxidase cannot oxidize D-glucose to any significant extent. For example, it has been hypothesized that arginine 330 (R330) may be important for hydrogen bonding of GAO and 0-4 of D-galactose, and that steric hindrance may prevent this bond forming between GAO and glucose (Ito, N., et al. (1991) Nature 350, 87–90).

For general literature describing GAO, its structure, and its enzyme activity, see Bibliography section entitled "GAO Literature."

Galactose oxidase is currently used mainly for assays of D-galactose and D-galactosamine. The enzyme oxidizes the hydroxyl group in the substrate to an aldehyde, which is reactive. Therefore, the enzyme is implicated for use in production of non-natural sugars and derivatives of sugars (Arts, S. J. H. F., et al. (1997), Synthesis, June 1997, 597–613; Kosman, D. J. (1984), in Lontie, R., Eds., Copper proteins and copper enzymes, Vol. 2., CRC Press, Boca Raton, Fla., 1–26; Root, R. L., et al. (1985) J. Am. Chem. Soc. 107, 2997–2999; Mazur, A. W., and Hiler, G. D. (1997) J. Org. Chem. 62, 4471–4475.; Martin, B. D., et al. (1998), Biomaterials, 19(1–3), 69–76). The Fusarium NRRL 2903 galactose oxidase gene has been cloned (McPherson, M. J., et al. (1992), J. Biol. Chem., 267(12), 8146–8152) and expressed in *Escherichia coli* (Lis, M., and Kuramitsu, H. K. (1997), Antimicrob. Agents Chemother., 41(5), 999–1003).

GAO has been used in a wide variety of applications, ranging from analytical and food chemistry to chemoenzymatic synthesis and clinical testing. For example, biological sensors based on GAO have been developed to determine the content of galactose (Tkac, J., et al. (1999) Biotechnology Techniques 13, 931–936), lactose and other GAO substrates (Vega, F. A., et al. (1998) Anal. Chim. Acta 373, 57–62) in biological samples. Such biosensors have also been used for quality control in dairy industries (Adanyi, N., et al. (1999) European Food Research and Technology 209, 220–226; Mannino, S., et al. (1999) Italian Journal of Food Science 11, 57–65), online bioprocess monitoring (Szabo, E. E., et al. (1996) Biosensors & Bioelectronics 11, 1051–1058) and analysis of blood samples of patients with suspected galactosemia (Vrbova, E., et al. (1992) Collection of Czechoslovak Chemical Communications 57, 2287–2294). Additionally, GAO is also used for the detection of the disaccharide D-galactose-beta-(1→3)-N-acetyl-galactosamine (Gal-GalNAc), a tumor marker in colonic cancer and precancer, and provides a cost-effective screening test for patients with neoplasia or at the risk of developing neoplasia (Yang, G. Y., and Shamsuddin, A. M. (1996) Histol. Histopathol. 11, 801–806; Said, I. T., et al., (1999) Histol. Histopathol. 14, 351–357).

GAO has also found applications in food chemistry, for example, in oxidized guar manufacture (Marrs, B. L. in IBC's Fifth Annual World Congress on Enzyme Technologies (2000) Las Vegas, Nev.) and to treat the oligosaccharide fraction contained in honey (Martin, I. G., et al. (1998) Food Chemistry 61, 281–286). Additionally, GAO has been used to oxidize the cell surface polysaccharides of membrane-bound glycoproteins containing terminal non-reducing galactose residues: this is an essential step in the successful radiolabeling of these glycoconjugates (Calderhead, D. M., and Lienhard, G. E. (1988) J. Biol. Chem. 263, 12171–12174; Gahmberg, C. G., and Tolvanen, M. (1994) Methods Enzymol. 230, 32–44).

The stereospecificity and substrate specificity of GAO have been exploited in the chemoenzymatic synthesis of L-sugars from polyols (Root, R. L., et al. (1985) J. Am. Chem. Soc. 107, 2997–2999), which are usually difficult to prepare by chemical methods (Dahlhoff, W. V., et al. (1980) Angew. Chem. Int. Ed. Engl. 19, 546–547; Koster, R., et al. (1982) Synthesis, 650–652). GAO has also been used to make sugar-containing polyamines (Liu, X. C., and Dordick, J. S. (1999) J. Am. Chem. Soc. 121, 466–467) and 5-C-(hydroxymethyl) hexoses (Mazur, A. W., and Hiler, G. D. (1997) J. Org. Chem. 62, 4471–4475).

In spite of its attractive properties and broad applicability, GAO applications in synthesis have been limited by a relatively low activity toward a large number of primary alcohols (Arts et al. (1997) Synthesis-Stuttgart 6, 597–610). The normal range of substrate specificity of GAO enzymes hampers its use for various practical applications. For example, a galactose oxidase showing activity towards new substrates such as polymeric materials and glucose would be desirable. However, previous attempts to engineer GAO to improve its activity towards D-glucose have met with difficulties, as no mutant with sufficiently improved activity towards D-glucose could be found (Sun, L., et al. (2001) Protein Eng. 14, 699–704).

Thus, there is a need to develop GAO enzymes with improved substrate specificity towards useful substrates. For example, there is a need for variant GAO enzymes with an improved ability to oxidize the 6-hydroxyl group of D-glucose. The invention addresses these and other needs in the art.

SUMMARY OF THE INVENTION

The present invention is based on the discovery of GAO mutants that are capable of oxidizing glucose and other alcohols that typically are not GAO substrates. Mutants that modify or improve enzymatic activity or specificity for such substrates, and methods of making such mutants, are also within the scope of the invention.

Accordingly, the present invention provides an isolated enzyme comprising a variant of a parent galactose oxidase, the parent having at least 70% sequence identity to SEQ ID NO:2, and the variant having a mutation in at least one amino acid residue positioned no more than 15 Å from a metal ion in the catalytic center of the parent, and an improved ability to oxidize D-glucose or a D-glucose derivative as compared to the parent. Preferably, the parent galactose oxidase is a *Fusarium* galactose oxidase. In one embodiment, the amino acid residue is positioned no more than 10 Å from a metal ion in the catalytic center of the parent. In another embodiment, the amino acid residue is positioned no more than 7 Å from a metal ion in the catalytic center of the parent. Preferably, the amino acid residue is an amino acid residue corresponding to a member of the group consisting of R330, Q406, W290, and Y329. The mutation can be, but is not limited to, a member of the group consisting of R330K, Q406S, Q406T, W290F, and Y329R. In a particular embodiment, the enzyme further comprises at least one mutation corresponding to a member of the group consisting of V494A, S10P, M70V, G195E, and N535D. The enzyme may have at least a 10-fold, preferably at least 50-fold, and most preferably at least 100-fold, higher capability to oxidize D-glucose than the parent enzyme. The improved ability to oxidize D-glucose is preferably a higher activity for oxidizing the 6-hydroxyl group of D-glucose.

The invention also provides for an isolated enzyme comprising a variant of a parent galactose oxidase, the parent having at least 70% sequence identity to SEQ ID NO:2, and the variant having a mutation in at least one amino acid residue positioned no more than 15 Å from a metal ion in the catalytic center of the parent, and an improved ability to oxidize a secondary alcohol-group as compared to the parent. Preferably, the parent galactose oxidase is a *Fusarium* galactose oxidase. In particular embodiments, the amino acid residue may positioned no more than 10 Å or 7

Å from a metal ion in the catalytic center of the parent. The amino acid residue may, for example, correspond to a member of the group consisting of R330, Q406, W290, and Y329. Exemplary, non-limiting, mutations include R330K, Q406S, Q406T, W290F, and Y329R. In one embodiment, the enzyme further comprises at least one mutation corresponding to a member of the group consisting of V494A, S10P, M70V, G195E, and N535D. The secondary alcohol can be, for example, an alcohol substituent of a substrate selected from the group consisting of 4-pyridylcarbinol, 2-propanol, 2-buten-2-ol, 2-octanol and 3,3 dimethyl 2-butanol.

The invention also provides for a method of producing a glucose-6 oxidase comprising the steps of: (a) constructing a library of variants of a parent galactose oxidase; and (b) selecting any variant having improved glucose-6 oxidation activity as compared to the parent galactose oxidase, wherein the library comprises variants having different mutations in a first amino acid residue positioned no more than 15 Å from a metal ion in the catalytic center of the parent galactose oxidase. In one embodiment, the library is produced by saturation mutagenesis. The parent galactose oxidase can have at least 70%, preferably at least 80%, and most preferably at least 90%, sequence identity to SEQ ID NO:2. The first amino acid residue can also be positioned no more than 10 Å or 7 Å from the metal ion. For example, the first amino acid residue can correspond to an amino acid residue of *Fusarium* GAO selected from R330, Q406, F464, W290, and Y329. The method can further comprise recombining a selected first variant having a mutation in the first amino acid residue with a second variant of the parent galactose oxidase having a mutation in a second amino acid residue. In this embodiment, the second variant can have an improved glucose-6 oxidation activity as compared to the parent galactose oxidase. Preferably, any selected galactose oxidase variant has at least 10 times, preferably at least 100 times, the glucose-6 oxidation activity of the parent galactose oxidase. In another embodiment, the first and second amino acid residues correspond to *Fusarium* GAO amino acid residues which are members of the group consisting of R330, Q406, F464, W290, and Y329.

The above features and many other attendant advantages of the invention will become better understood by reference to the following detailed description when taken in conjunction with the accompanying drawings.

DETAILED DESCRIPTION OF THE INVENTION

Figure 1:
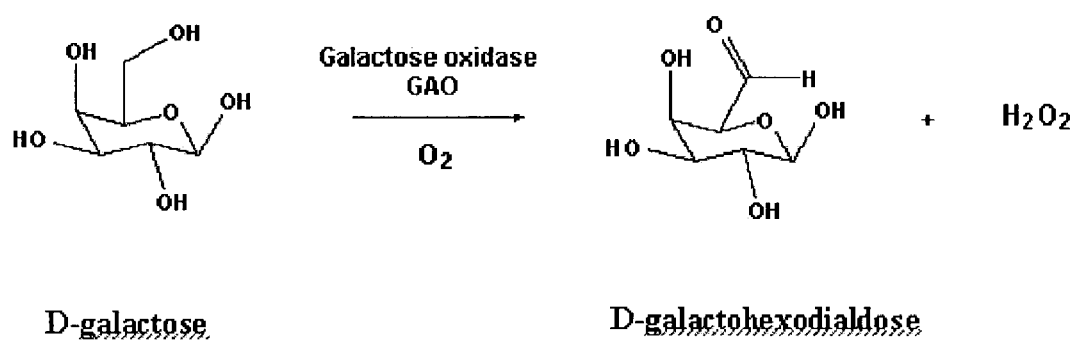
FIG. 1 shows a typical wild-type GAO reaction scheme in which D-galactose is oxidized to produce a D-galactohexodialdose product, in the presence of galactose oxidase (GAO) enzyme.

This invention provides enzymes produced by mutagenesis that have a modified substrate activity and/or specificity, and/or an altered or improved enzymatic function. For example, wild-type GAO catalyzes the oxidation of the 6-hydroxyl group of D-galactose and D-galactose-derivatives (Amaral, D. et al. (1963) J. Biol. Chem., 238, 2281–2284; see FIG. 1), and is only a catalyst for primary alcohols. A substrate of particular interest, D-glucose, has been found to be an extremely poor or de minimus substrate for GAO. The oxidation rate for the 6-hydroxyl group of glucose, when detectable, is about a half-million fold lower than that for D-galactose, and no other enzymes are known to be capable of selectively oxidizing the 6-hydroxyl group of D-glucose. In a study where random mutagenesis was applied to engineer GAO to improve expression in bacteria, attempts were also made to improve GAO activity towards D-glucose. However, no mutant with improved activity towards D-glucose was found (Sun, L., et al. (2001) Protein Eng. 14, 699–704).

The present invention has solved these problems by modifying wild-type *Fusarium* GAO or other GAO enzymes, particularly those capable of oxidizing the 6-hydroxyl group of D-galactose, to provide glucose oxidase enzymes, particularly glucose-6 oxidases, and enzymes having improved activity or specificity for secondary alcohols. Specifically, a saturation mutagenesis library of proteins mutated at particular combinations of amino acid sites was generated. From this library, novel GAO variants were identified that selectively oxidize a different set of substrates, exemplified by glucose and its 6-hydroxyl group. Substrates for which GAO mutants exhibit improved activity include monocarbohydrates, oligocarbohydrates, polycarbohydrates, aliphatic primary alcohols, aliphatic secondary alcohols and aromatic alcohols, including, but not limited to, D-glucose, 2-deoxy-D-glucose, β-methyl-D-gluco-pyranoside, α-methyl-D-gluco-pyranoside, D-mannose, L-galactose, amylose, starch, α-cellulose, 2-butanol, 2-propanol, 2–3-buten-2-ol, and 2-pyridylcarbinol. While wild-type GAO, under some circumstances, may exhibit a detectable oxidation of these substrates, the GAO variants or mutants are significantly more efficient.

Preferred GAO mutants comprise mutations at one or more of the amino acid residues set forth in Table 1A. Each mutation refers to specific amino acid residues in SEQ ID NO:2 (assigning the first methionine residue of SEQ ID NO:2 as position zero). The GAO variants of the invention preferably comprise amino acid substitutions of at least one, preferably of at least two, and even more of preferably at least three of the amino acid residues set forth in Table 1A. Thus, a preferred GAO variant can comprise mutations at amino acid residues W290, R330, Q406, and/or Y329. Most preferably, the amino acid substitutions at these residues are W290F, R330K, Q406S, Q406T, and/or Y329R. Also contemplated and encompassed by the present invention are amino acid mutations at these positions which are function-conservative to the aforementioned amino acid substitutions. For example, an amino acid characterized by a hydrophobic side chain may be substituted for another amino acid with a hydrophobic side chain. Examples of function conservative substitutions are W290T and R330H because an aromatic and basic amino acid has been replaced by another aromatic and basic amino acid, respectively.

The GAO of the invention may also be designed from a wild-type GAO, or another GAO mutant. In one embodiment, the mutant GAOs of the invention comprise, in addition to at least one of the mutations in Table 1A, one or more of the mutations in the GAO mutant denoted A3.E7, described in WO 01/88110, WO 01/62938, Sun et al. (2001) Protein Eng. 14, 699–704 and in the Examples. The A3.E7 mutations are V494A (T1481C), S10P (T28C), M70V (A208G), G195E (G584A), N535D (A1603G) of SEQ ID NO:2 (and SEQ ID NO:1, respectively) and a silent mutation at P136 (T408C). These mutations, as well as sequence- and function-conservative variants of these mutations, provide high-level expression and improved stability as compared to wild-type GAO (WO 01/88110, Sun et al. (2001) Protein Eng. 14, 699–704).

TABLE 1A

Exemplary GAO Mutation Sites and Mutations for Improving Substrate Specificity

| Amino Acid Residues of SEQ ID NO: 2 | Amino Acid Substituion | Nucleotide Substitution |
|---|---|---|
| W290 | W290F | TGG→TTC |
| R330 | R330K | CGT→AAG |
| Q406 | Q406S | CAA→AGC |
|  | Q406T | CAA→ACG |
| Y329 | Y329R | TAC→CGC |

In addition, the invention provides GAO mutants having specific nucleic acid and amino acid sequences. The nucleic acid sequences include those which encode the GAO variants in Table 1B. The amino acid sequences include those which have the combinations of amino acid mutations in Table 1B, where all mutations refer to SEQ ID No:2, the first methionine being at position zero.

TABLE 1B

Preferred GAO Variants

| Mutant | Amino Acid Mutations in SEQ ID NO: 2 | Activity Towards D-Glucose As Compared to A3.E7 |
|---|---|---|
| 1 | R330K, Q406T, V494A, S10P, P136, M70V, G195E, N535D | >20× |
| 2 | R330K, Q406S, V494A, S10P, P136, M70V, G195E, N535D | >20× |
| 3 | W290F, V494A, S10P, P136, M70V, G195E, N535D | >10× |

TABLE 1B-continued

Preferred GAO Variants

| Mutant | Amino Acid Mutations in SEQ ID NO: 2 | Activity Towards D-Glucose As Compared to A3.E7 |
|---|---|---|
| 4 (RQW) | R330K, Q406T, W290F, V494A, S10P, P136, M70V, G195E, N535D | >100× |
| 5 | R330K, Q406T, W290F, V494A, S10P, P136, M70V, G195E, N535D, Y329R | >200× |

The invention provides novel enzyme variants that have a higher ability to oxidize glucose and/or other alcohols than the corresponding parent or wild-type enzyme. In particular, one may construct a variant based on the sequence of any wild-type or mutant enzyme by aligning its amino acid sequence with SEQ ID NO:2 and identifying any residue or residues that align with those of Table 1A and/or Table 1B, such as residues that align with any of W290, R330, and/or Q406 of SEQ ID NO:2. Once those residues have been identified, appropriate amino acid substitutions can be made in the parent sequence to derive a variant in accordance with the present invention. Preferably, the novel variants have the same or a higher capability to oxidize the 6-hydroxyl group of glucose or another alcohol than the wild-type or parent enzyme.

Preferably, the mutation in the GAO sequence results in a W→F or T, R→K or H, or a Q→S or T substitution at the amino acid residues aligned with SEQ ID NO:2 residues W290, R330, and Q406, respectively. Preferred, non-limiting examples of wild-type sequences that can be used to create such novel variants include glyoxal oxidase (GenBank Accession No. AAA33747, Kersten, P. J. and Cullen, D. (1993) Proc. Natl. Acad. Sci. USA, 90, 7411–7413); and fbfb (CAA77680; Silakowski, B, Ehret, H. and Schairer, H. U. (1998), J. Bacteriol. 1241–1247). Glyoxal oxidase has a notably similar active center residues as in GAO. Preferred, non-limiting examples of GAO variants that can be used to create such novel variants include A1.D2, A1.C11, A1.D12, A2.D3, A2.C3, A2.D6, A2.E12, B1.D4, B2.G4, B3.H7 and B4.F12 (described in WO 01/88110 and in Sun et al. (2001) Protein Eng. 14, 699–704). These GAO variants comprise various combinations of the following amino acid substitutions: N537D, V494A, C515S, V494A, S10P, G195E, N535D, M70V, and N413D. In one embodiment, enzymes that are 70% identical to wild-type GAO or variants of GAO (e.g. A3-E7 and A1.D2) are used to design such novel variants. In another embodiment, enzymes that are 80% identical or 90% identical, or 95% identical to wild-type GAO or GAO variants (such as those disclosed in WO 01/88110 and in Sun et al. (2001) Protein Eng. 14 699–704) are used to design the novel variants.

According to the invention, novel glucose 6-oxidase enzymes can be created by, for example, saturation mutagenesis of particular residues of GAO. It will be understood that other mutagenesis techniques may be used. Preferred mutant GAO enzymes not only demonstrate an improved activity towards D-glucose, but can also exhibit improved activity towards secondary alcohols, as well as other compounds (see Tables 4A and 4B in the Examples).

The present invention also provides a method to design novel glucose-6 oxidases. For example, a novel glucose-6-oxidase can be prepared by (a) selecting one or more amino acid residues that, in a 3-D model of a galactose oxidase active site, are within 15 Å, 10 Å, or 7 Å, of a metal ion in the catalytic center of the enzyme, (b) conducting saturation mutagenesis of at least one of the selected residues, and (c) screening or identifying GAO variants that have at least ×10, more preferably at least ×50, and most preferably at least ×10 times the glucose-6 oxidation activity of the GAO parent. If desired, two or more identified variants can be recombined to further improve glucose-6 oxidation. In *Fusarium* GAO, particularly the *Fusarium* GAO having the amino acid sequence of SEQ ID NO:2, the metal ion is Cu(II), and amino acid residues within 15 Å of the Cu(II) include I169, V170, P171, A172, A173, A174, M185, W186, S187, S188, Y189, R190, N191, D192, A193, F194, G195, G196, S197, I201, T202, L203, H224, D225, M226, F227, C228, P229, G230, I231, V241, T242, G243, G244, N245, D264, A247, R270, G271, Y272, Q273, S274, S275, G287, G288, S291, G292, G293, V294, K297, D324, Q326, G327, L328, Y329, R330, S331, D332, D333, H334, A335, W336, P350, A381, M382, C383, G384, N385, S402, D404, T440, F441, H442, T443, G457, R460, G461, I462, P463, F464, E465, D466, V492, R493, V494, Y495, S497, I498, S499, G510, G511, G512, G513, L514, C515, G516, D517, C518, T520, N521, H522, T578, A579, T580, H581, T582, V583, and A584; amino acid residues within 10 Å include A172, A173, S187, S188, A193, F194, G195, M226, F227, C228, P229, G244, N245, G271, Y272, W290, Y329, R330, N333, H334, C383, Y405, Q406, F441, P463, F464, V494, Y495, H496, S497, G512, G513, L514, C515, T580, H581, and T582; and amino acid residues within 7 Å include A172, F194, F227, C228, Y272, W290, R330, H334, Y405, F464, Y495, Y496, G513, T580 and H581. In the Examples, R330, Q406, F464, W290, and Y329 were subjected to saturation mutagenesis and the resulting variants screened for glucose-6 oxidation activity, thereby leading to the identification of novel glucose-6 oxidases. The method of the invention can also be used for designing variants of GAO enzymes that are capable of oxidizing alcohols, including secondary alcohols, by applying a screening method for such substrates (see Examples).

The selection of a GAO for modification into a glucose-6 oxidase or an enzyme capable of oxidizing, for example, secondary alcohols can be made based on significant sequence identity and/or significant structural similarity in the active site to Fusarium GAO or to SEQ ID NO:2. For example, in one embodiment, a GAO is selected in which the amino acid sequence encompassing both the first and last amino acid residues within 15 Å, 10 Å, or 7 Å of the metal ion in the active center is at least 70%, more preferably 80%, and even more preferably at least 90% identical to a sequence of SEQ ID NO:2. As is known in the art, whenever two proteins have amino acids that can be aligned with statistical significance, they will also have super-imposable tertiary structures (Kyte J., In: Structure in Protein Chemistry, Garland Publishing Inc., New York & London 1995, pp. 243–278).

A novel GAO that is capable of oxidizing the 6-hydroxyl group of glucose has many practical applications and advantages. For example, a D-glucose oxidizing GAO may be used as a biological sensor to determine glucose levels. Alternatively, such an enzyme may also be used to diagnose hyperglycemia in diabetic patients. Glucose-oxidizing GAO could also be used in many food and material processes to synthesize new or improved products. In addition, glucose-oxidizing GAO could be used to synthesize carbohydrate compounds such as carbohydrate-based antibiotics and vaccines, and to improve properties of pulps or other carbohydrate-based materials in the paper processing industry.

The improved activity of the novel GAOs towards additional new substrates, including D-glucose derivatives, L-galactose, and aliphatic secondary alcohols such as 2-butanol, 2-propanol and 3-buten-2-ol, 3,3-dimethyl-2-butanol, and 2-octanol also has important applications. These novel variants provide new and improved applications of the enzyme in organic synthesis, sensor applications, and other areas. For chemical synthesis applications, selective oxidation of secondary alcohols to the corresponding ketones may avoid the use of protecting groups, minimize side reactions often observed in traditional chemical synthesis, and would be a more environmentally friendly process. Use of variant GAO enzymes as a synthetic reagent would facilitate the use of more inexpensive, safe and biodegradable carbohydrate materials in industrial processes (Mazur, A. in Enzymes in Carbohydrate Synthesis (1991) Bednarski, M. D. and Simon, E. S. Eds., pp. 99–110).

A more efficient enzyme is expected to be advantageous in the food chemistry applications of GAO, and, in particular in the selective modification of guar and other carbohydrate-based polymers. GAO variants according to the invention would also be useful for modification of carbohydrate-based (e.g., cellulose-based) textiles and other materials. The aldehyde function produced by the GAO could be used to couple other substances selectively at the modified position on the polymer.

Definitions

The following defined terms are used throughout the present specification, and should be helpful in understanding the scope and practice of the present invention.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

The term "substrate" means any substance or compound that is converted or meant to be converted into another compound by or with the help of the action of an enzyme catalyst. Exemplary substrates include aromatic and aliphatic compounds, and include not only a single compound, but also combinations of compounds, such as solutions, mixtures and other materials that contain at least one substrate. Preferred substrates according to the invention include, but are not limited to, glucose and glucose derivatives, and secondary alcohols such as 2-butanol. The term "derivative" refers to the addition, deletion or substitution of one or more functional groups such as, e.g., alcohol-, amine-, halogen-, thiol-, amide-, and carboxyl-groups, to a molecule.

"Glucose" is an aldohexose in which the hydroxyl groups attached to the second, fourth, and fifth carbon atoms can be regarded as being on the same side of the molecule when it is represented as a linear structure.

A "glucose derivative" herein means an aldohexose or an aldohexose polymer in which the hydroxyl groups attached to the fourth and fifth carbon atoms can be regarded as being on the same side of the molecule when it is represented as a linear structure (i.e. open form). Optionally, one or more groups of the aldohexose other than the hydroxyl group of carbon 6 may be deleted, modified, or added to the glucose derivative. Non-limiting examples of glucose derivatives are 2-deoxy-D-glucose, methyl-β-D-gluco-pyranoside, methyl-α-D-gluco-pyranoside, methyl-α-D-manno pyranosides, methyl-β-D-manno-pyranosides, D-mannoses, a D-maltoses, and alkylated and/or halogenated aldohexoses.

An "oxidation reaction" or "oxygenation reaction", as used herein, is a chemical or biochemical reaction involving the addition of oxygen to a substrate, to form an oxygenated or oxidized substrate or product. An oxidation reaction is typically accompanied by a reduction reaction (hence the term "redox" reaction, for oxidation and reduction). A compound is "oxidized" when it receives oxygen or loses electrons. A compound is "reduced" when it loses oxygen or gains electrons. Wild-type GAO typically catalyzes the oxidation of a primary alcohol group of a substrate (e.g., galactose) to an aldehyde (e.g., galactohexodialdase). FIG. 1. Mutant GAO enzymes of the invention selectively catalyze a different oxidation reaction, e.g., the oxidation of glucose or a secondary alcohol group of a substrate to a corresponding aldehyde or ketone.

A "polypeptide" (one or more peptides) is a chain of chemical building blocks called amino acids that are linked together by chemical bonds called peptide bonds. A protein or polypeptide, including an enzyme, may be "native" or "wild-type", meaning that it occurs in nature or has the amino acid sequence of a native protein, respectively. These terms are sometimes used interchangeably. A polypeptide may or may not be glycosylated. A "recombinant wild-type" typically means a wild-type sequence produced by a recombinant host without glycosylation. Sequence comparisons in the examples and figures of this application are generally with reference to a wild type that is a recombinant wild type. A polypeptide may also be a "mutant", "variant" or "modified", meaning that it has been made, altered, derived, or is in some way different or changed from a wild-type, native or parent protein, or from another mutant. A mutant or modified protein or enzyme is usually, although not necessarily, expressed from a mutant polynucleotide or gene. A native or wild-type protein comprises the natural sequence of amino acids in the polypeptide, however produced or obtained, and typically includes glycosylation in nature, but may or may not be glycosylated as used herein.

A "parent" polypeptide or enzyme is any polypeptide or enzyme from which any other polypeptide or enzyme is derived or made, using any methods, tools or techniques, and whether or not the parent is itself a native or mutant polypeptide or enzyme. A parent polynucleotide is one that encodes a parent polypeptide.

Proteins and enzymes are made in cells, including host cells using instructions in DNA and RNA, according to the genetic code. Generally, a DNA sequence having instructions for a particular protein or enzyme is "transcribed" into a corresponding sequence of RNA. The RNA sequence in turn is "translated" into the sequence of amino acids that form the protein or enzyme. An "amino acid sequence" is any chain of two or more amino acids. One or more triplets of nucleotides in DNA or RNA represent each amino acid. For example, the amino acid lysine (Lys) can be coded by the nucleotide triplet or codon AAA or by the codon AAG. (The genetic code has some redundancy, also called degeneracy, meaning that most amino acids have more than one corresponding codon.) Because the nucleotides in DNA and RNA sequences are read in groups of three for protein production, it is important to begin reading the sequence at the correct amino acid, so that the correct triplets are read. The way that a nucleotide sequence is grouped into codons is called the "reading frame."

An "enzyme" means any substance, preferably composed wholly or largely of protein, that catalyzes or promotes, more or less specifically, one or more chemical or biochemical reactions. The term "enzyme" can also refer to a catalytic polynucleotide (e.g., RNA or DNA).

An "oxidation enzyme" is an enzyme that catalyzes one or more oxidation reactions, typically by adding, inserting, contributing or transferring oxygen from a source or donor to a substrate. Such enzymes are also called oxidoreductases or redox enzymes, and encompasses oxygenases, hydrogenases or reductases, oxidases and peroxidases.

The terms "oxygen donor", "oxidizing agent" and "oxidant" mean a substance, molecule or compound that donates oxygen to a substrate in an oxidation reaction. Typically, the oxygen donor is reduced (accepts electrons). Exemplary oxygen donors, which are not limiting, include molecular oxygen or dioxygen ($O_2$) and peroxides, including alkyl peroxides such as t-butyl peroxide, and most preferably hydrogen peroxide (H2O2). A peroxide is any compound having two oxygen atoms bound to each other.

A "galactose oxidase" enzyme means an enzyme capable of selectively, specifically, or preferentially promoting the conversion of the 6-hydroxyl-group of galactose substrate to a corresponding aldehyde-group.

A "glucose 6-oxidase" enzyme means an enzyme capable of selectively, specifically, or preferentially promoting the conversion of the primary 6-hydroxyl-group of a glucose substrate into a corresponding aldehyde group.

A "mutation" means any process or mechanism resulting in a mutant protein, enzyme, polypeptide, polynucleotide, gene, or cell. This includes any mutation in which a protein, enzyme, polynucleotide, or gene sequence is altered, and any detectable change in a cell arising from such a mutation. The altered protein, enzyme, polypeptide or polynucleotide is a "mutant", also called a "variant." Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon. Table 2 outlines which amino acids correspond to which codon(s).

The terms "mutant" and "variant" may also be used to indicate a modified or altered gene, DNA sequence, enzyme, cell, etc., i.e., any kind of mutant. Such changes also include changes in the promoter, ribosome binding site, etc.

TABLE 2

Amino Acids, Corresponding Codons, and Functionality/Property

| Amino Acid | SLC | DNA codons | Side Chain Property |
|---|---|---|---|
| Isoleucine | I | ATT, ATC, ATA | Hydrophobic |
| Leucine | L | CTT, CTC, CTA, CTG, TTA, TTG | Hydrophobic |
| Valine | V | GTT, GTC, GTA, GTG | Hydrophobic |
| Phenylalanine | F | TTT, TTC | Aromatic side chain |
| Methionine | M | ATG | Sulphur group |
| Cysteine | C | TGT, TGC | Sulphur group |
| Alanine | A | GCT, GCC, GCA, GCG | Hydrophobic |

TABLE 2-continued

Amino Acids, Corresponding Codons, and Functionality/Property

| Amino Acid | SLC | DNA codons | Side Chain Property |
|---|---|---|---|
| Glycine | G | GGT, GGC, GGA, GGG | Hydrophobic |
| Proline | P | CCT, CCC, CCA, CCG | Secondary amine |
| Threonine | T | ACT, ACC, ACA, ACG | Aliphatic hydroxyl |
| Serine | S | TCT, TCC, TCA, TCG, AGT, AGC | Aliphatic hydroxyl |
| Tyrosine | T | TAT, TAC | Aromatic side chain |
| Tryptophan | W | TGG | Aromatic side chain |
| Glutamine | Q | CAA, CAG | Amide group |
| Asparagine | N | AAT, AAC | Amide group |
| Histidine | H | CAT, CAC | Basic side chain |
| Glutamic acid | E | GAA, GAG | Acidic side chain |
| Aspartic Acid | D | GAT, GAC | Acidic side chain |
| Lysine | K | AAA, AAG | Basic side chain |
| Arginine | R | CGT, CGC, CGA, CGG, AGA, AGG | Basic side chain |
| Stop codons | Stop | TAA, TAG, TGA | — |

"Function-conservative variants" are proteins or enzymes in which a given amino acid residue has been changed without altering the overall structural conformation and specified function of the protein or enzyme. This includes but is not limited to, replacement of an amino acid with one having similar structural or physical properties, including polar or non-polar character, size, shape and charge (see, e.g., Table 2).

As referred to herein, "sequence similarity" means the extent to which nucleotide or protein sequences are related. The extent of similarity between two sequences can be based on percent sequence identity and/or conservation. Amino acids other than those indicated as conserved may differ in a protein or enzyme so that the percent protein or amino acid sequence similarity between any two proteins of similar function may vary and can be, for example, at least 30%, preferably at least 50%, more preferably at least 70%, even more preferably 80%, and most preferably at least 90%, as determined according to an alignment scheme.

"Sequence identity" herein means the extent to which two nucleotide or amino acid sequences are invariant.

"Sequence alignment" means the process of lining up two or more sequences to achieve maximal levels of sequence identity (and, in the case of amino acid sequences, conservation), e.g., for the purpose of assessing the degree of sequence similarity. Numerous methods for aligning sequences and assessing similarity and/or identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that result in the highest sequence similarity.

A "saturation mutagenesis library" is a library of variants of a parent protein, wherein each variant protein has a mutation in the same amino acid residue.

The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. Preferred activity units for expressing activity include the catalytic constant ($k_{cat}=V_{max}/E$; $V_{max}$ is maximal turnover rate; E is concentration of enzyme); the Michaelis-Menten constant ($K_m$); and $k_{cat}/K_m$. These units can be determined using well-established methods in the art of enzyme assays.

The "specificity" of an enzyme is defined by the range of molecules that serve as substrates, and the relative preference of an enzyme for at least one substrate compared to at lest one other substrate.

The "stability" or "resistance" of an enzyme means its ability to function, over time, in a particular environment or under particular conditions. One way to evaluate stability or resistance is to assess its ability to resist a loss of activity over time, under given conditions. Enzyme stability can also be evaluated in other ways, for example, by determining the relative degree to which the enzyme is in a folded or unfolded state. Thus, one enzyme has improved stability or resistance over another enzyme when it is more resistant than the other enzyme to a loss of activity under the same conditions, is more resistant to unfolding, or is more durable by any suitable measure. For example, a more "organic-solvent" resistant enzyme is one that is more resistant to loss of structure (unfolding) or function (enzyme activity) when exposed to an organic solvent, and a more "thermostable" enzyme is one that is more resistant to loss of structure (unfolding) or function (enzyme activity) when exposed to higher temperatures.

The "catalytic center" in an enzyme or enzyme variant is the site in the enzyme where the substrate or substrates attach and gets converted to the product or products of the enzymatically catalyzed reaction. In the case of certain galactose oxidases and galactose oxidase variants, the catalytic center contains a metal ion such as a Cu(II) ion.

The term "polymer" means any substance or compound that is composed of two or more building blocks ('mers') that are repetitively linked to each other. For example, a "dimer" is a compound in which two building blocks have been joined together.

Molecular Biology

In accordance with the present invention there may be employed conventional molecular biology, microbiology, and recombinant DNA techniques within the skill of the art. The general genetic engineering tools and techniques discussed herein, including transformation and expression, the use of host cells, vectors, expression systems, etc., are well known in the art. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al. 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994). The term "host cell" means any cell of any organism that is selected, modified, transformed, grown, or used or manipulated in any way, for the production of a substance by the cell, for example the expression by the cell of a gene, a DNA or RNA sequence, a protein or an enzyme.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions, and the like, and may be modified by many means known in the art. Non-limiting examples of such modifications include methylation, "caps", substitution of one or more of the naturally occurring nucleotides with an analog, and inter-nucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A "coding sequence" or a sequence "encoding" a polypeptide, protein or enzyme is a nucleotide sequence that, when expressed, results in the production of that polypeptide, protein or enzyme, i.e., the nucleotide sequence encodes an amino acid sequence for that polypeptide, protein or enzyme. Preferably, the coding sequence is a double-stranded DNA sequence that is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining this invention, the promoter sequence is bounded at its 3' terminus by the transcription initiation site and extends upstream (5' direction) to include the minimum number of bases or elements necessary to initiate transcription at levels detectable above background. As described above, promoter DNA is a DNA sequence which initiates, regulates, or otherwise mediates or controls the expression of the coding DNA. A promoter may be "inducible", meaning that it is influenced by the presence or amount of another compound (an "inducer"). For example, an inducible promoter includes those that initiate or increase the expression of a downstream coding sequence in the presence of a particular inducer compound. A "leaky" inducible promoter is a promoter that provides a high expression level in the presence of an inducer compound and a comparatively very low expression level, and at minimum a detectable expression level, in the absence of the inducer.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence, which may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct."

A common type of vector is a "plasmid", which generally is a self-contained molecule of double-stranded DNA. A plasmid can readily accept additional (foreign) DNA and which can readily be introduced into a suitable host cell. A plasmid vector often contains coding DNA and promoter DNA and has one or more restriction sites suitable for inserting foreign DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clontech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes. Routine experimentation in biotechnology can be used to determine which vectors are best suited for used with the invention. In general, the choice of vector depends on the size of the polynucleotide sequence and the host cells to be used.

The term "expression system" means a host cell and compatible vector under suitable conditions, e.g. for the expression of a protein coded for by foreign DNA carried by the vector and introduced to the host cell. Common expression systems include bacteria (e.g. *E. coli* and *B. subtilis*) or yeast (e.g. *S. cerevisiae*) host cells and plasmid vectors, and insect host cells and Baculovirus vectors. As used herein, a "facile expression system" means any expression system that is foreign or heterologous to a selected polynucleotide or polypeptide, and which employs host cells that can be grown or maintained more advantageously than cells that are native or heterologous to the selected polynucleotide or polypeptide, or which can produce the polypeptide more efficiently or in higher yield. For example, the use of robust prokaryotic cells to express a protein of eukaryotic origin would be a facile expression system. Preferred facile expression systems include *E. coli*, *B. subtilis* and *S. cerevisiae* host cells and any suitable vector.

"Sequence-conservative variants" of a polynucleotide sequence are those in which a change of one or more nucleotides in a given codon position results in no alteration in the amino acid encoded at that position.

The term "DNA reassembly" is used when recombination occurs between identical sequences. "DNA shuffling" refers to a group of in vitro or in vivo methods involving recombination of nucleic acid species. For example, homologous recombination of pools of nucleic acid fragments or polynucleotides can be employed to generate polynucleotide molecules having variant sequences of the invention. Such methods can be employed to generate polynucleotide molecules having variant sequences of the invention.

"Isolation" or "purification" of a polypeptide or enzyme refers to the derivation of the polypeptide by removing it from its original environment (for example, from its natural environment if it is naturally occurring, or form the host cell if it is produced by recombinant DNA methods). Methods for polypeptide purification are well known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the protein or against peptides derived therefrom can be used as purification reagents. Other purification methods are possible. A purified polynucleotide or polypeptide may contain less than about 50%, preferably less than about 75%, and most preferably less than about 90%, of the cellular components with which it was originally associated. A "substantially pure" enzyme indicates the highest degree of purity that can be achieved using conventional purification techniques known in the art.

Polynucleotides are "hybridizable" to each other when at least one strand of one polynucleotide can anneal to another polynucleotide under defined stringency conditions. Stringency of hybridization is determined, e.g., by the temperature at which hybridization and/or washing is performed, and b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences. (1×SSC is 0.15 M NaCl, 0.015 M Na citrate.) Polynucleotides that "hybridize" to the polynucleotides herein may be of any length. In one embodiment, such polynucleotides are at least 10, preferably at least 15 and most preferably at least 20 nucleotides long. In another embodiment, polynucleotides that hybridizes are of about the same length. In another embodiment, polynucleotides that hybridize include those which anneal under suitable stringency conditions and which encode polypeptides or enzymes having the same function, such as the ability to catalyze an oxidation, oxygenase, or coupling reaction of the invention.

Designing Novel Galactose Oxidases

The novel galactose oxidases, characterized by novel substrate specificity and/or activity, can be generated by various mutagenesis methods, including the ones described below. For example, variants of galactose oxidase that are capable of oxidizing D-glucose can be generated by directed evolution, random point mutagenesis or by site-directed mutagenesis. The generated variants are tested for their activity towards galactose, glucose and other substrates. Variants that demonstrate the desired characteristics (such as increased ability to oxidize glucose) can be further mutated in order to optimize desired characteristics. Combinations of mutations at different sites and combinations of different residues at previously identified sites can also be tested in order to optimize oxidase activity and substrate specificity.

Generation of such novel galactose oxidase variants or mutants results in the production of novel enzymes, with novel activity and/or substrate specificity. These mutants also illustrate the residues that are important or essential for galactose binding.

According to the method of the invention, amino acid residues in or near the active site of a GAO enzyme can be selected and exposed to various mutagenesis techniques, e.g., site-directed mutagenesis and/or saturation mutagenesis, to generate novel GAO enzymes which have improved activity towards selected substrates such as D-glucose.

In one embodiment, the method involves (a) selecting amino, acid residues that, in a 3-D model of the active site of a galactose oxidase, lies within 15 Å, 10 Å, or 7 Å, of a metal ion in the catalytic center of the enzyme, (b) mutating at least one of the selected residues, and (c) screening or identifying GAO variants that have at least ×10, more preferably at least ×50, even more preferably at least ×100, and most preferably at least ×200 times the activity of the GAO parent in converting a selected substrate to the desired product. If desired, two or more identified variants can be recombined to further improve glucose-6 oxidation, as described in the Examples.

To construct a 3-D model of a galactose oxidase, any method known in the art can be employed. For example, Baron et al. (J Biol Chem 1994;269:25095) describe characterization of the active site structure of *Fusarium* GAO and Y272, C228, and W290 mutants thereof, by crystallizing each protein using a standard protocol, and collecting diffraction data. Ito et al. (Nature 1991;350;87–90) also provide crystallization protocols and 3-D structures of *Fusarium* GAO.

In a particular embodiment, the GAO variant of the invention comprises a metal-coordinated active site having at least one amino acid that corresponds, by alignment with the amino acid sequence of SEQ ID NO:2, to amino acids C228, Y272, Y495, H496, and H581, or having at least one amino acid that corresponds, by alignment with the amino acid sequence of SEQ ID NO:2, to amino acids F194, α290, β330, γ406, and F464, wherein α is one of F and T, β is one of K and H, and γ is one of S and T and wherein the enzyme catalyzes the oxidation of a secondary alcohol or a glucose derivative. The secondary alcohol can be selected from the group consisting 4-pyridylcarbinol, 2-propanol, 2-buten-2-ol, 2-octanol, and 3,3-dimethyl 2-butanol. The glucose derivative can be selected from the group consisting of 2-deoxy-D-glucose, methyl-α-D-gluco-pyranoside, methyl-β-D-gluco-pyranoside, methyl-α-N-manno-pyranoside, methyl-β-D-manno-pyranoside, D-mannose and D-maltose. In a further embodiment, the enzyme can further comprise at least one amino acid mutation in a residue corresponding to A494, P10, V70, E195, or D535.

Mutating a selected amino acid residue in the active site region can be accomplished using any known technique, including those listed in the section entitled "Mutagenesis Techniques." Saturation mutagenesis is a preferred, although non-limiting, method for this purpose.

The screening method is chosen based on the particular substrate or product to detect. Methods for detecting various substrates and/or products are provided in the Examples, and in the section entitled "Screening Methods" below.

Mutagenesis Techniques

General methods for producing mutant proteins (also described as "variant proteins" herein) according to the invention using directed evolution and other techniques are described briefly below and more extensively, for example, in U.S. Pat. Nos. 5,741,691 and 5,811,238. See also, International Applications WO 98/42832, WO 95/22625, WO 97/20078, and U.S. Pat. Nos. 5,605,793 and 5,830,721. Any known method for generating mutations in a native or parent polynucleotide sequence to provide variant or evolved polynucleotides for expression in expression systems can be employed. Proteins produced by such methods can be screened for improved activity, specificity and other functions and properties according to conventional methods.

Any source of nucleic acid in purified form can be utilized as the starting or parent nucleic acid. In one embodiment, the starting nucleic acid is a wild-type nucleic acid corresponding to a gene encoding a galactose oxidase. Thus the process may employ DNA or RNA including messenger RNA, which DNA or RNA may be single or double stranded. The nucleic acid sequence may be of various lengths depending on the size of the nucleic acid sequence to be mutated. Preferably the specific nucleic acid sequence is from 50 to 50,000 base pairs. It is contemplated that entire vectors containing the nucleic acid encoding the protein of interest may be used to generate the products of this invention.

The following sections describe some of the mutagenesis techniques that can be employed to generate the products of the invention.

Error-prone PCR is a well-known technique relying on, for example, the intrinsic infidelity of Taq-based PCR, which can be used to mutate or mutagenize a mixture of fragments of unknown sequences (Caldwell, R. C.; Joyce, G. F. PCR Methods Applic. 2, 28 (1992).; Leung, D. W. et al. Technique 1, (1989); Gramm, H. et al. Proc. Natl. Acad. Sci. USA 89, 3576 (1992)).

Cassette mutagenesis (Stemmer, W. P. C. et al. Biotechniques 14, 256 (1992); Arkin, A. and Youvan, D. C. Proc. Natl. Acad. Sci. USA 89, 7811 (1992); Oliphant, A. R. et al. Gene 44, 177 (1986); Hermes, J. D. et al. Proc. Natl. Acad. Sci. USA 87, 696 (1990); Delagrave et al. Protein Engineering 6, 327 (1993); Delagrave et al. Bio/Technology 11, 1548 (1993); Goldman, E. R. and Youvan D. C. Bio/Technology 10,1557 (1992)), is a technique in which the specific region optimized is replaced with a synthetically mutagenized oligonucleotide. These techniques can also be employed under low-fidelity polymerization conditions to introduce a low level of point mutations randomly over a long sequence, or to mutagenize a mixture of fragments of unknown sequence.

Oligonucleotide-directed mutagenesis, which replaces a short sequence with a synthetically mutagenized oligonucleotide, may also be employed to generate evolved polynucleotides having improved expression or novel substrate specificity.

Alternatively, nucleic acid shuffling, which uses a method of in vitro or in vivo, generally homologous, recombination of pools of nucleic acid fragments or polynucleotides, can be employed to generate polynucleotide molecules having variant sequences of the invention.

The polynucleotide sequences for use in the invention can also be altered by chemical mutagenesis. Chemical mutagens include, for example, sodium bisulfite, nitrous acid, hydroxylamine, hydrazine or formic acid. Other agents that are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light, or by subjecting the polynucleotide to propagation in a host (such as *E. coli*) that is deficient in the normal DNA damage repair function. Generally, plasmid DNA or DNA fragments so mutagenized are introduced into *E. coli* and propagated as a pool or library of mutant plasmids.

In particular, where there are regions of known or suspected importance for an enzyme activity or property, saturation mutagenesis has proven useful to generate mutants with improved functions. In this technique, a pool of mutants with all possible amino acid substitutions at one or more residues of interest is generated, and mutants with desired properties are isolated by an efficient selection or screening procedure (Miyazaki, K. and Arnold, F. H. (1999) J. Mol. Evol. 49, 716–720. Howitz, M. S. and Loeb, L. A. (1986). Proc. Natl. Acad. Sci. USA. 83, 7406–7409). Commercially available kits, such as the QuikChange® Site-Directed Mutagenesis kit (Stratagene) can be used to carry out saturation mutagenesis. The QuikChange® kit allows for point mutations to be made without performing error-prone PCR, thus allowing for a high degree of accuracy. A "saturation mutagenesis library" is a library of variants of a parent protein, wherein each variant protein has a mutation in the same amino acid residue.

Once the variant polynucleotide molecules have been generated, they can be cloned into a suitable vector selected by the skilled artisan according to methods well known in the art. If a mixed population of the specific nucleic acid sequence is cloned into a vector, it can be clonally amplified by inserting each vector into a host cell and allowing the host cell to amplify and express the vector. The mutant enzymes can be expressed in conventional or facile expression systems such as *E. Coli*, and are readily isolated and purified from the expression system or media if secreted. A mixed population of expressed polypeptides may be screened to identify desired recombinant nucleic acid fragments. The screening method will depend on the desired property sought after. For example, in this invention a DNA fragment that encodes a modified GAO enzyme can be screened for substrate specificity and activity of the enzyme. Such tests are well known in the art, and are exemplified below.

Thus, using various methods for mutagenesis, the invention provides a means for producing novel, functional GAO proteins with improved activity toward one or more substrates, preferably D-glucose or secondary alcohols.

Screening and Activity Assays

The phrase "screening assay" refers to an assay that can be used to screen a multitude of enzyme variants, usually in parallel, to identify those exhibiting an improved selected activity. The phrase "activity assay" refers to an experiment or assay which determines the oxidase activity of an enzyme, e.g., GAO or a variant of GAO, towards one or more substrates, such as galactose or D-glucose, either as a particular parameter ($V_{max}$, $k_{cat}$, etc.) or in relation to a wild-type enzyme or a standard value. Frequently, the same principles can be applied to screening and activity assays, which may differ mainly in the methods used for detecting remaining substrate or product formed.

"Galactose oxidase activity" refers here to the activity of a given GAO enzyme or variant for any given substrate, such as galactose or D-glucose. The particular substrate and corresponding enzymatic activity may be stated or it may be inferred, e.g., by context. If no other substrate or activity is specifically stated or implied, the commonly understood meaning of "galactose oxidase activity" is the ability of the enzyme to catalyze the oxidation of galactose.

GAO can generate equimolar amounts of hydrogen peroxide and oxidation product by oxidation of a substrate. Colorimetric detection of hydrogen peroxide can therefore be used to assay galactose oxidase activity by employing the following reaction scheme:

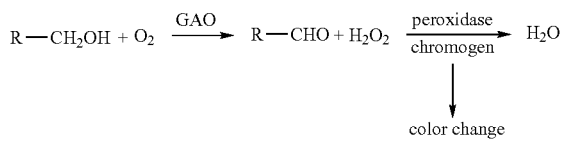

This system can be used to assay for oxidation of various substrates, with a very high sensitivity. In the reaction scheme above, an alcohol group of a substrate R is oxidized to produce an aldehyde and hydrogen peroxide ($H_2O_2$) is released. For example, D-galactose is converted to D-galactohexodialdose plus $H_2O_2$. The chromogen, in the presence of hydrogen peroxide and peroxidase enzyme, e.g. horseradish peroxidase (HRP), produces a detectable color change, indicating that the reaction catalyzed by GAO has occurred.

Many aromatic compounds can be used as a chromogen for the assay. Four chromogens show particularly strong color formation; green, orange, red and red, respectively: (a) 2,2'-azinobis(3-ethylbenzothiazoline-6-sulfonic acid) (ABTS) (Baron, A. J., et al. (1994) J. Biol. Chem. 269, 25095–25105); (b) o-anisidine; (c) o-dianisidine (Lis, M., and Kuramitsu, H. K. (1997) Antimicrob. Agents Chemother., 41(5), 999–1003; Tressel, P. S., and Kosman, D. J. (1989), Methods Enzymol., 89, 163–171; Koroleva, O. V. et al. (1983), Prikl. Biokhim. Mikrobiol., 19(5), 632–637; Avigad, G. (1985), Arch. Biochem. Biophys., 239(2), 531–537) and (d) o-tolidine (Maradufu, A., et al. (1974), Carbohydr. Res. 32, 93–99; Kosman, D. J. (1984), in Lontie, R., Eds., Copper proteins and copper enzymes. Vol. 2., CRC Press, Boca Raton, Fla., 1–26). Their peaks of absorbance are 410 nm, 490 nm, 460 nm and 420 nm. ABTS is a preferred chromogen for these types of assays, since ABTS forms its color most strongly and sensitively. Moreover, the highest assay sensitivity and lowest background was achieved when using a 100 mM sodium phosphate buffer solution (pH 7.0) for the assay.

Other galactose oxidase screening techniques and/or activity assays, have the following advantages: high specificity for galactose oxidase, high sensitivity, good reproducibility, quantitative measurements, simplicity, flexibility for many substrates, and low cost. One screening system utilizes microplates and the other utilizes membranes. Both systems apply horseradish peroxidase (type I, Sigma) together with a chromogen (ABTS).

The microplate assay has a high sensitivity. Moreover, the enzyme activity can be determined quantitatively. To increase throughput, the method can be automated, for example robotically. This method is particularly suitable as a second screen, after active clones are identified by a more rapid first screen, such as a membrane screen (see below). In experiments using these procedures, the active cultures on the microplate having galactose oxidase activity are indicated by strong green color formation, where each positive well on the microplate is visible as a dark circle. GAO activity was screened in 96-well plates.

Briefly, single colonies are picked from LB-Ampicillin (LB-Amp) agar plates into deep-well plates and grown in LB-Amp. The master plates were duplicated into new deep-well plates containing LB-Amp-1 mM IPTG. Following cultivation at 30° C., CuSO4 is added and the cells are lysed with lysozyme and SDS. Cell extracts are reacted with galactose and allyl alcohol using the GAO-HRP coupled assay.

Although microplate screening is highly sensitivity and quantitative, it is desirable to provide a method that contemporaneously assays many more, e.g., thousands more clones in a sensitive, accurate, practical and efficient manner. Methods for detecting galactose oxidase activities directly from colonies on agar-plate can be used, but may exhibit relatively low sensitivity, low reproducibility, and very slow color formation. To evaluate very large number of mutants, activities can be detected directly (e.g., visually), or detected by transferring colonies transferred to a membrane. These methods are based on colorimetric detection using chromogen and peroxidase, as in the microplate screening system.

A suitable screening method using membranes has been developed, as is shown here in one optimized form. After transformants formed colonies on an LB-Amp plate (100 mg/l at 30° C. for 18–24 hours), these colonies were transferred to a membrane, i.e., they were adsorbed onto the membrane and lifted. A suitable membrane is Immobilon NC (HATF), surfactant-free, 45 mm, 82 mm (Millipore). For cultivation, the membrane was placed on a new LB-Amp plate (100 mg/l) and was incubated at 30° C. until new colonies were formed on the membrane (6–12 hours). The membrane then was transferred to a new LB-Amp (100 mg/l ) plate with 1 mM IPTG, at 30° C. for 6 hours, for induction. Then, the membrane was put on a filter paper at room temperature, containing lysozyme (0.5 mg/ml), D-galactose (100 mM), ABTS (2 mg/ml), peroxidase (10 units/ml) and $CuSO_4$ (0.4 mM). In experiments using these procedures, colonies with galactose oxidase activity showed as deep purple on the filter paper.

This simple method has suitable sensitivity and can be used to evaluate several thousands colonies at once. The membrane screening method can be used with an image analyzer, for quantitative determination of activity of each colony. Although the sensitivity of this method is not as high as others, the method is fast and is suitable for a first or initial screening, because many thousands or even millions of colonies can be contemporaneously or rapidly evaluated.

In a preferred embodiment, galactose oxidase activities of colonies that are transferred to a membrane are estimated directly. Colonies, which are formed on LB-Ampicillin plate at 30° C. for 24 hours, are transferred onto a membrane (Immobilon NC (HATF), surfactant-free, 45 mm, 82 mm, Millipore). The membrane is put on a new LB-Ampicillin plate and is kept at 30° C. for 6~12 hours until colonies are re-formed. Then the membrane is transferred onto an LB-Ampicillin plate containing 1 mM IPTG and is incubated for 6 hours at 30° C. After the membrane is put on filter paper containing 0.5 mg/l lysozyme, 100 mM substrate, 2 mg/ml ABTS, 10 units/ml peroxidase and 0.4 mM CuSO4 in 100 mM sodium phosphate buffer solution (pH 7.0), the membrane is kept at room temperature for one day, covered with a shield (ABTS is light sensitive). Active colonies show deep purple color formations.

Copper sulfate is used to provide copper (II) ion to activate the recombinant (mutant or variant) enzyme. The activity of partially purified galactose oxidase from D. dendroides (Sigma) was detected well by using peroxidase and ABTS as described; the addition of copper (II) ion and other cofactors was not needed. (The Sigma enzyme already includes copper ions.) However, experiments with cell-free extracts of recombinant GAO enzymes of the invention showed that almost no activity was detected in the absence of copper (II) ions. Thus, the presence of copper (II) ion is preferred, and without being bound by any theory, is believed to be essential, to activate recombinant GAO enzymes produced by E. coli as described herein. Treatment with copper ions at 4° C. is preferred. Copper ion can be provided as copper sulfate ($CuSO_4$). Experiments showed that 0.1 mM $CuSO_4$ is sufficient, whereas 10 mM $CuSO_4$ slightly inhibited GAO activity. Experiments under assay conditions showed that the preferred concentration of CuSO4 for activating crude enzyme solution is 0.4 mM. The metal (II) ions of iron, cobalt, nickel, and manganese, and the metal chelator EDTA, did not affect activation of the recombinant GAO in experiments under assay conditions.

In certain assay embodiments, sodium azide or sodium sulfide may be added, for example in an amount of from about 0.01 mM to less than 1 mM. These reagents may enhance detection of GAO activity in some circumstances.

Addition of detergents to the assay solution also increased the observed activity. Pretreatment with SDS is most effective for increasing the galactose oxidase activity. Treatment with SDS for longer than 12 hours at 4° C. after treatment with lysozyme is suitable for the assay. Other detergents may also be used.

It will be understood by persons of ordinary skill in the art that assays described herein for determining the ability of an enzyme to oxidize a galactose can be readily adapted to determine the ability of an enzyme to oxidize glucose.

EXAMPLES

The following Example(s) are understood to be exemplary only, and do not limit the scope of the invention or the appended claims. A person of ordinary skill in the art will appreciate that the invention can be practiced in many forms according to the claims and disclosures here.

Example 1

Conversion of Galactose Oxidase Into a Glucose 6-Oxidase

No known enzymes catalyze the selective oxidation of the 6-hydroxyl group of D-glucose to introduce an aldehyde functionality. A synthetically useful reaction such as selective functionalization at the glucose C-6 position in oligo- and polysaccharides would greatly facilitate further chemical modifications for food, pharmaceutical and materials applications.

In the present Example, the fungal enzyme galactose oxidase was selected as a starting point to generate the first known glucose 6-oxidase enzymes. The new enzymes exhibit broader substrate specificity compared to a wild-type counterpart. The mutants can oxidize secondary or aliphatic alcohols to produce the corresponding ketones. Characterization of the oxidation product of a methyl-β-D-glucosepyranoside shows that the 6-hydroxyl group was oxidized to generate an aldehyde.

A well-characterized copper-containing radical enzyme, GAO oxidizes various primary alcohols to their corresponding aldehydes, with the reduction of oxygen to hydrogen peroxide (Cooper, J., et al. (1959), J. Biol. Chem., 234–445.; Amaral, D., et al. (1963) J. Biol. Chem., 238, 2281–2284.; Ito, N., et al. (1991) Nature 350, 87–90.; Whitaker, M. W., and Whitaker, J. W. (1988) J. Biol. Chem. 263, 6074–6080.; Baron, A. J., et al. (1994) J. Biol. Chem. 269, 25095–25105).

Highly active towards the 6-OH of D-galactose, native GAO is essentially inactive towards D-glucose. Glucose apparently cannot bind at the active site, as concentrations as high as 1 M have no effect on the enzyme's activity towards D-galactose (Wachter, R. and Branchaud, B., (1996), J. Am. Chem. Soc., 118, 2782).

Directed Evolution

Initially, an attempt was made to generate activity towards D-glucose by random point mutagenesis of wild-type *Fusarium* GAO and mutant A3.E7. After screening more than 30,000 clones, however, no improvement in D-glucose activity was observed, although both the enzyme expression level and thermostability were enhanced (Sun, L., et al. (2001) Protein Eng. 14, 699–704; see also WO 01/88110). The GAO variant exhibiting the most favorable expression and stability features, termed A3.E7, had the following mutations in the wild-type GAO sequence (SEQ ID NO:2): V494A (T1481C), S10P (T28C), M70V (A208G), G195E (G584A), N535D (A1603G) and a silent mutation at P136 (T408C). Careful examination of the GAO activity of A3.E7 however, showed that it was at least 1 million-fold less active on D-glucose than on D-galactose. Therefore it was concluded that this novel activity would require significant remodeling of the active site and would not be accessible by point mutagenesis.

Active Site Remodeling

Figure 2A:
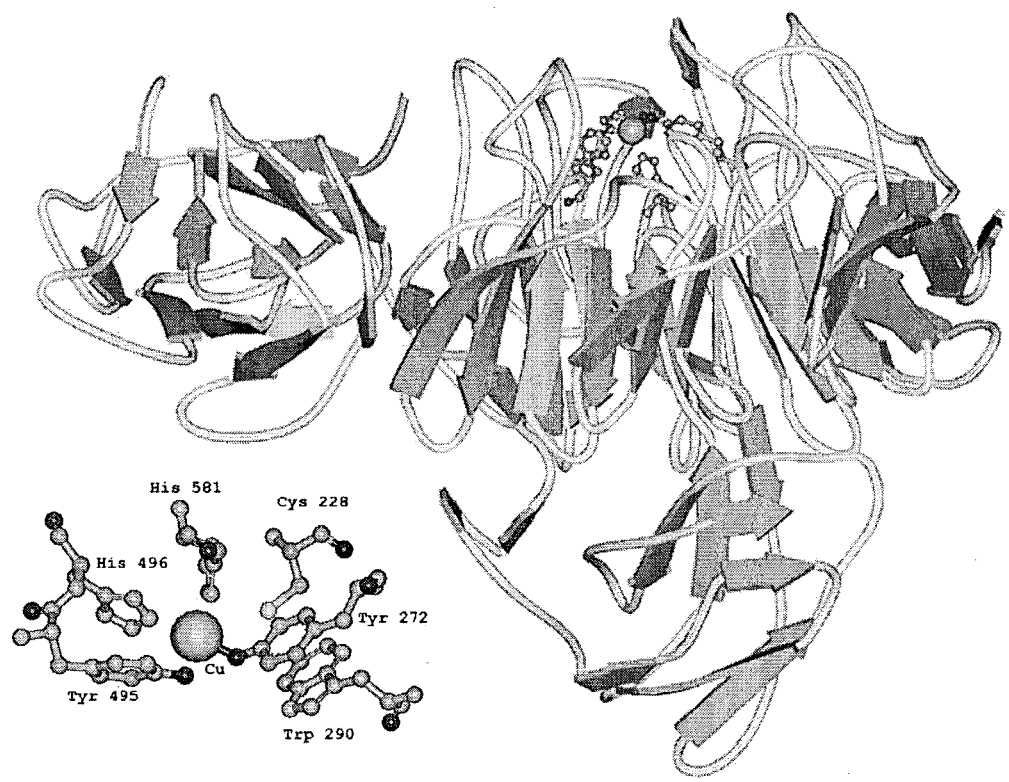
FIG. 2 shows a 3-D structure of GAO and its active site. (A) The location of the active site in GAO, and a view of certain key residues in the active site. (B) Alternative view of the GAO active site, showing residues subjected to saturation mutagenesis in Example 1 (R330, Q406, F464, F194, and W290). See, Baron, A. J., et al. (1994) J. Biol. Chem. 269, 25095–25105; Ito, N. et al. (1991) Nature 350, 87–90.
Figure 2B:
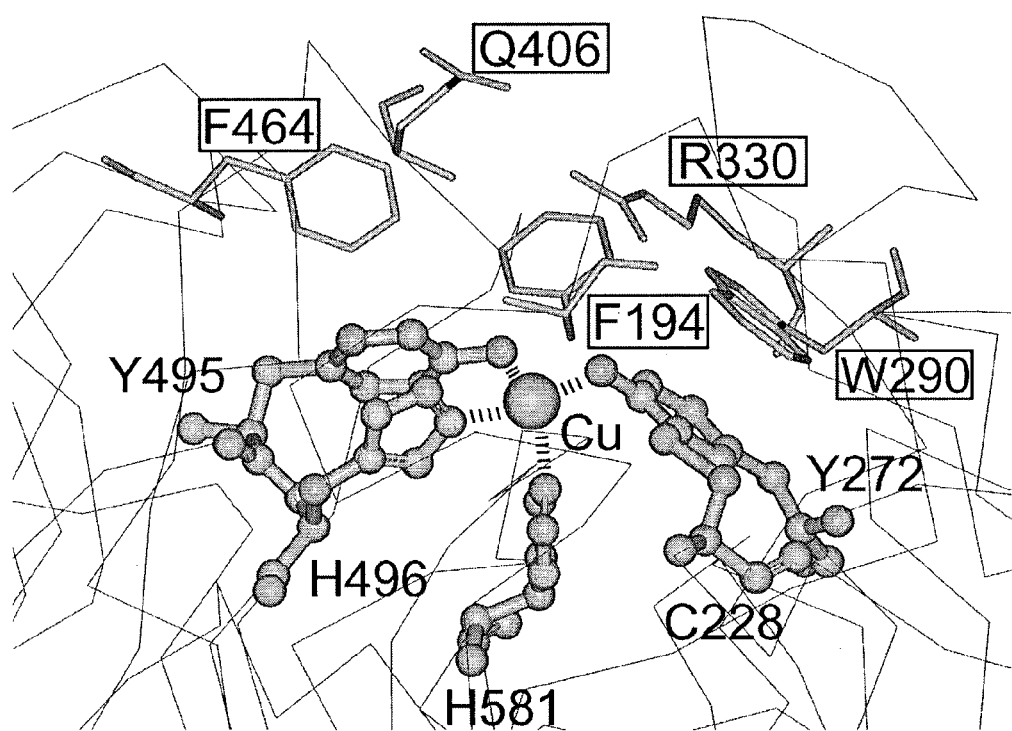

The three-dimensional crystal structure of GAO has been reported and a substrate binding model has been proposed based on a molecular docking experiment (Ito, N., et al. (1991) Nature 350, 87–90.; Baron, A. J., et al. (1994) J. Biol. Chem. 269, 25095–25105; Ito, N., et al. (1994) J. Mol. Biol. 238, 794–814). (See FIG. 2.) According to the model, the water-accessible surface calculation revealed a pocket at the copper site that is structurally complementary to D-galactose in its chair conformation. This mode of substrate binding suggested favorable interaction between the enzyme and substrate. Arg-330 forms hydrogen bonds with the hydroxyl groups of substrate C(4) and C(3), while Gln-406 forms an additional hydrogen bond with the C(2) hydroxyl. In addition, a hydrophobic wall of the pocket containing Phe-194 and Phe-464 interacts with the D-galactose backbone (C(6), C(5) and C(4)). Trp-290, which has been proposed to stabilize the radical of GAO (Baron, A. J. et al. (1994) J. Biol. Chem. 269, 25095–25105), is believed to play a key role in restricting entry to the active center (FIG. 2)(Saysell, C. G., et al. (1997), JBIC, 2, 702–709).

Based on the above information, saturation mutagenesis was applied at specific amino acid residues of mutant A3.E7. The A3.E7 galactose oxidase variant was effectively expressed and had increased thermostability, accordingly, it was chosen as a starting point for the generation of a glucose 6-oxidase. The resulting libraries were screened for activity towards D-galactose and D-glucose.

Materials and Methods

All chemicals were reagent grade or better. 2,2'-Azinobis(3-ethylbenzthiazoline-6-sulfonic acid) (ABTS), D-galactose and horseradish peroxidase (HRP) were from Sigma (St. Louis, Mo.). *E. coli* strain BL21(DE3) was purchased from Novagen (Madison, Wis.) and plasmid pGAO-36 containing GAO mutant A3.E7 was described previously (Sun, L., et al. (2001) Protein Eng. 14, 699–704). Restriction enzymes and ligase were obtained from Boehringer Mannheim (Indianapolis, Ind.), Life Technologies (Grand Island, N.Y.) or New England Biolabs (Beverly, Mass.). Site-directed mutagenesis kit (QuikChange®) was purchased from Stratagene (La Jolla, Calif.).

Library Construction and Screening

The library Lib-RFQ containing random mutations at three sites (R330, Q406 and F464) was constructed using QuikChange® kit (Stratagene) according to the manufacturer's instructions, using A3.E7 as parent enzyme. The primers used in constructing the libraries are listed in Table 3. The underlined sections in the primers indicate that alternative sequences can be used ("N" can be any one of A, C, G, and T, and G/C means that G or C can be used).

TABLE 3

Nucleotide primers

| Nucleotide Sequence[1] | SEQ ID NO: |
|---|---|
| GCT GAC AAG CAA GGA TTG TAC NN(G/C) TCA GAC AAC CAC GCG TGG | 3 |
| CCA CGC GTG GTT GTC TGA (G/C)NN GTA CAA TCC TTG CTT GTC AGC (for Lib-R). | 4 |
| GGC CAA CGA CGT ATT CCG NN(G/C) GAG GAT TCA ACC CCG | 5 |
| CGG GGT TGA ATC CTC (G/C)NN CGG AAT TCC ACG TCG TTG GCC (for Lib-RF), | 6 |
| GGT TGT GGC GTC AGA GTC (G/C)NN ATA ATC TGG GGA GGC GGC | 7 |
| GCC GCC TCC CCA GAT TAT NN(G/C) GAC TCT GAC GCC ACA ACC (for Lib-RFQ) | 8 |
| GCG GTC TTC ATA TCG CAA TGA TGC ANN (G/C)GA AGG ATC CCC TGG TGG | 9 |
| CAA CCA GGG GAT CCT TC(G/C) NNT GCA TCA TTG CGA TAT GAA GAC CAC (for Lib-RFQF), | 10 |
| CCA TTG GAG GCT CCN N(G/C)A GCG GTG GCG TAT TTG AGA AGA ATG GCG | 11 |
| CGC CAT TCT TCT CAA ATA CGC CAC CGC T(G/C)N NGG AGC CTC CAA TGG (for Lib-W) | 12 |

[1]Sequences are in 5' to 3' direction unless otherwise indicated

PCR conditions were as follows: 95° C. for 30 s, 18 cycles of 95° C. for 30 seconds, 55° C. for 60 seconds and 68° C. for 9.5 min. The PCR products were digested by DpnI. Then the mixtures were purified by Qiagen PCR purification kit before being transformed by electroporation into BL21 (DE3) cells. The transformation and cell cultivation were described previously (Sun, L., et al. (2001) Protein Eng. 14, 699–704).

Screening Assay for D-Galactose and D-Glucose

*E. coli* strain BL21(DE3) harboring galactose oxidase mutants was plated on LB-agarose-ampicillin plates and incubated overnight at 30° C. Single colonies were picked into 96-well plates containing 200 µl of LB containing 100 82 g/L ampicillin and the culture was cultivated in a shaking incubator at 30° C. and 250 rpm for 12 hours. The master plates were duplicated by transferring a 10 μl aliquot to a new deep-well plate containing 300 μl LB-Amp and grown for 12 h at 30° C. and 250 rpm. The cultures were then centrifuged for 5 minutes at 4000 rpm and the cell pellet was re-suspended in 300 μl 100 mM sodium phosphate (NaPi) buffer, pH 7.0, containing 0.4 mM $CuSO_4$. The cell solution was then treated by 0.5 mg/ml lysozyme (2 hours at 30° C.). After transferring 80 μl of the cell solution into 320 μl of sodium phosphate buffer (100 mM, pH 7.0) containing 0.4 mM $CuSO_4$ and 0.125% (w/v) SDS, the cell solutions were incubated at 4° C. overnight.

Aliquots of the cell extracts were reacted with D-galactose and D-glucose at pH 7.0. The initial rate (for D-galactose activity assay) or endpoint (for D-glucose activity assay) of $H_2O_2$ formation was recorded by monitoring the horseradish peroxidase (HRP)-catalyzed oxidation of ABTS at 405 nm on a Thermomax microplate reader (Molecular Devices, Sunnyvale, Calif.).

Protein Purification and Characterization

*E. coli* cultivation and the cell disruption were performed as previously described (Sun, L. et al. (2001) Protein Eng. 14, 699–704). BL21(DE3) harboring wildtype and mutant galactose oxidase were cultivated in 1 L of LB-ampicillin (100 μg/ml) 12 hours at 30° C. in a shaking incubator. Cells were harvested by centrifugation (4000×g, 15 minutes) and re-suspended in 100 mM sodium phosphate buffer, pH 7.0 (5 g cells/10 ml). After the cells were disrupted by sonication, the cell debris was removed by centrifugation and the resulting supernatant was incubated with 0.4 mM $CuSO_4$ for 2 hours at 4° C. The samples (15 ml solution from 5 g of cells) were then loaded onto a DEAE-cellulose column and eluted with 50 mM NaPi, pH 7.0 at 4° C. The active fractions were pooled and concentrated in a stirred ultrafiltration cell (Amicon Corp., Beverly, Mass.). The concentrated samples were dialyzed against 10 mM NaPi, pH 7.3, overnight and was loaded into a cellulose phosphate column. After washing with 500 ml of NaPi (10 mM, pH 7.3), the samples were further eluted with a linear gradient of 270 ml of 10 mM+270 ml of 100 mM NaPi, pH 7.3. The active fractions were collected and concentrated by ultrafiltration. The concentrated samples were dialyzed against 100 mM NaPi pH 7.0 overnight prior to storage at −80° C. The purified protein ran as a single band during SDS-PAGE (Novex, San Diego, Calif.). Protein concentrations were determined from the absorbance at 280 nm ($\epsilon=1.05\times10^5$ $M^{-1}cm^{-1}$) and corrected by a factor of 16/15 (Baron, A. J. et al. (1994) J. Biol. Chem. 269, 25095–25105) for the M-RQW.

Activity Assay: Oxidation of Methyl-β-D-Galacto-Pyranoside, Methyl-β-D-Gluco-Pyranoside and 2-Butanol Oxidation reaction. Oxidation of methyl-β-D-galacto-pyranoside with Sigma GAO was performed in 5 ml NaPi (50 mM, pH 7.0) with 300 mM substrate, 95 U of Sigma GAO, 700 U catalase (Sigma) and 0.5 mM copper ion. Oxidation of methyl-β-D-gluco-pyranoside with M-RQW was performed in 2 ml of NaPi (50 mM, pH 7.0) with 200 mM substrate, 1.8 U mutant, 1700 U catalase and 0.5 mM copper ion. Both reactions were performed at room temperature with vigorous stirring. 2-Butanol oxidation by M-RQW was performed at room temperature in 100 μl NaPi (50 mM, pH 7.0) containing 50 mM substrate, 0.5 mM copper ion, 0.9 U mutant GAO and 150 U catalase.

Gas chromatography-mass spectrometry analysis of 2-butanol oxidation reaction. Gas chromatography-mass spectrometry (GC-MS) analysis was performed on an HP 6890 series GC system with HP 5973 mass selective detector and Rtx-1 column (60 m×0.3 mm×5 cm, Restek, Belletontane, Pa.). Helium was used as the carrier gas with the flow rate 1 ml/min. The mass spectrometer was operated in the scan mode (8.17 scans/sec) for the mass range between 40 and 200 amu. The GC was temperature programmed as follows: initial temperature 70° C., then at 5° C./min to 100° C. and at 20° C./min to 200° C. The inlet and transfer line temperature were 200° C.

Thin layer chromatography and nuclear magnetic resonance analysis of the methyl-β-D-galacto-pyranoside and methyl-β-D-gluco-pyranoside oxidation products. Thin layer chromatography (TLC) was used to monitor the oxidation reactions. Chromatograms were developed on silica gel plates (250 cm, Whatman, Maidstone, Kent, England) using chloroform-methanol (4:1) as the solvent. The plates were dried before they were immersed into Bial's reagent (orcinol/ferric chloride with 3 volumes of ethanol) (Sigma) and visualized by heating at 120° C. for 5 min. Aldehydes were visualized by spraying the TLC plates with Purpald solution (2% in 1 M NaOH).

A silica gel column (40 cm flash, Baker, Phillipsburg, N.J.) was used to isolate the reaction products. The reaction mixtures were filtered using centrifugal filter devices (Millipore, Bedford, Mass.) to remove the enzymes. The filtered reaction mixtures (10 ml) were loaded into the column directly and eluted with chloroform-methanol (4:1) and the eluted fractions were checked with TLC plates. The fractions containing product were pooled and the solvent was evaporated. The crystallized samples were dissolved into D2O and stored at 4° C. Purpald reagent (Sigma) was used to monitor the formation of aldehydes (Hopps, H. B., (2000) Aldrichimica Acta, 33, 28).

$^1H$ 1D and 2D (COSY) nuclear magnetic resonance (NMR) spectra and $^{13}C$ NMR spectra were recorded on a Varian-500 instrument. $^1$H-NMR (500 MHz, D2O, 300K) of methyl-β-D-1,6-dialdehyde-gluco-pyranoside: d=5.28 (d, 1H, H-1), 4.4 (d, 1H, H-6), 3.6 (s, 3H, —$CH_3$), 3.52 (m, 2H, H-3, H-4), 3.42 (m, 1H, H-2), 3.29 (m, 1H, H-5) ¾ $^{13}C$ NMR (75 MHz, $D_2O$, 300K): $\delta_C$ 103.6 (C-1), 88.1 (C-6), 76.67 (C-5), 75.81 (C-3), 73.14 (C-2), 70.32 (C-4), 57.43 ($CH_3$).

Results and Discussion

A combinational library was constructed by saturation mutagenesis of Arg-330, Phe-464 and Gln-406 of GAO mutant A3.E7 that is expressed efficiently in *E. coli* (Sun, L. et al. (2001) Protein Eng. 14, 699–704).

The first saturation mutagenesis library contained mutations at three sites: R330, Q406 and F464. Residue R330 was subjected to saturation mutagenesis first using QuikChange® kit (Stratagene). Saturation mutagenesis at residue F464 was performed in the same way using the templates containing the mixture of the plasmids isolated from 100 clones from the R330 library. The final library (Lib-RFQ) was constructed by performing saturation mutagenesis on residue Q406 on the mixed plasmid templates of 2000 clones from the previous two-site library. The mutants identified from this library as having activity on glucose were subject to saturation mutagenesis at residue F194 to generate library Lib-RFQF. At the same time, another library (Lib-W290) was constructed by employing saturation mutagenesis at residue W290 using A3.E7 as the template. Then, the mutants isolated from these two libraries (Lib-RFQ and Lib-W290) that were identified as having activity on glucose were combined to generate the final mutants, using site-directed mutagenesis on the corresponding residues to introduce the mutations.

More than 10,000 clones were screened from library Lib-RFQ; >95% were inactive on galactose and none was more active than the parent. Two mutants with amino acid substitutions at R330 and Q406 were identified: R330K (CGT→AAG), Q406T (CAA→ACG) and R330K (CGT→AAG), Q406S (CAA→AGC). These mutants showed more than 20 times improved activity towards D-glucose and around 100 times decreased activity towards D-galactose. Further saturation mutagenesis on the residue of F194 did not result in an improved mutant. Screening of the library Lib-W290 led to the identification of a mutant with the amino acid substitution of W290F (TGG→TTC), which shows more than 10 times improved activity towards D-glucose. Again, no mutants with enhanced activity towards D-galactose were identified. Introduction of the mutation W290F into the mutant from the library Lib-RFQ generated a mutant (RQW) with three mutations, R330K, Q406T and W290F. This mutant shows approximately more than 100 times improved activity towards D-glucose and 1000 times decreased activity towards D-galactose compared to A3.E7. As expected, activity on glucose came at a significant cost to the enzymes natural activity towards galactose, which decreased 1,000 fold in M-RQW.

Mutant Characterization

The mutant RQW was purified for further characterization. The mutant RQW (R330K, Q406T and W290F in addition to the A3.E7 mutations) was purified by DEAE cellulose column chromatography and then on a cellulose phosphate column, as described above. The purified enzyme shows a single band when checked by SDS-PAGE.

The activity of wild-type (i.e., recombinantly produced *Fusarium* GAO) and mutant galactose oxidase towards various substrates were measured by monitoring the formation of hydrogen peroxide using an ABTS-HRP assay. The formation of a green product by this coupled assay was detected by an absorbance at 420 nm. The amount of wildtype enzyme varied from 0.38–3.8 μg in a 1 ml reaction. The amount of mutant enzyme varied from 0.5–5 μg in a 1 ml reaction. One unit of activity is the amount of enzyme that is able to produce 1 μmol of product per minute under the reaction conditions.

The substrate specificity (Tables 4A and 4B) of the mutant RQW revealed that it accepts not only the substrates of the native GAO, but also a number of new substrates, including novel monocarbohydrates, oligocarbohydrates, polycarbohydrates, aliphatic primary alcohols, aliphatic secondary alcohols and aromatic alcohols, including L-galactose, D-glucose and its derivatives as well as aliphatic secondary alcohols.

TABLE 4A

Substrate specificity of the wild-type (Fusarium GAO) and mutant (RQW) GAOs.
Substrate concentration is indicated within parentheses.

| Substrate Name | Substrate Structure | Wild-Type Activity (U/mg) | Mutant Activity (U/mg) |
| --- | --- | --- | --- |
| D-Galactose | | 122 (50 mM) | 9.42 (0.1 M) |
| D-Glucose | | 0 (1 M) | 1.93 (0.42 M) |
| 2-Deoxy-D-Glucose | | 0 (0.5 M) | 1.4 (0.25 M) |

TABLE 4A-continued

Substrate specificity of the wild-type (Fusarium GAO) and mutant (RQW) GAOs.
Substrate concentration is indicated within parentheses.

| Substrate Name | Substrate Structure | Wild-Type Activity (U/mg) | Mutant Activity (U/mg) |
| --- | --- | --- | --- |
| Methyl-α-D-Glucopyranoside | [structure] | 0 (50 mM) | 0.98 (0.42 M) |
| Methyl-β-D-Glucopyranoside | [structure] | 0 (1 M) | 1.32 (0.42 M) |
| D-Fucose | [structure] | 8.56 (50 mM) | $2.29 \times 10^{-3}$ (0.27 M) |
| D-Fructose | [structure] | 0 (1 M) | 8.10 (0.25 M) |
| Methyl-α-D-Mannopyranoside | [structure] | 0 (0.5 M) | 0.19 (0.42 M) |
| Methyl-β-D-Mannopyranoside | [structure] | 0 (1 M) | 0.683 (0.6 M) |
| D-Mannose | [structure] | 0 (1 M) | $6.83 \times 10^{-4}$ (0.25 M) |

TABLE 4A-continued

Substrate specificity of the wild-type (Fusarium GAO) and mutant (RQW) GAOs.
Substrate concentration is indicated within parentheses.

| Substrate Name | Substrate Structure | Wild-Type Activity (U/mg) | Mutant Activity (U/mg) |
| --- | --- | --- | --- |
| β-D-Lactose | | 58.3 (50 mM) | 6.76 (67.8 mM) |
| Methyl-α-D-Xylo-pyranoside | | 0 (1 M) | 0.34 (0.42 M) |
| Methyl-β-D-Arabino-pyranoside | | 0 (1 M) | 0.10 (0.42 M) |
| Methyl-β-D-Galacto-pyranoside | | 155 (50 mM) | 9.21 (0.1 M) |
| 2-Deoxy-D-Ribose | | 0 (50 mM) | $1.40 \times 10^{-4}$ (0.25 M) |
| L-Galactose | | 0 (50 mM) | 0.535 (0.25 M) |
| Allyl Alochol | | 0.946 (0.5 M) | 121 (50 mM) |

TABLE 4A-continued

Substrate specificity of the wild-type (Fusarium GAO) and mutant (RQW) GAOs.
Substrate concentration is indicated within parentheses.

| Substrate Name | Substrate Structure | Wild-Type Activity (U/mg) | Mutant Activity (U/mg) |
|---|---|---|---|
| D-Maltose | | 0 (0.25 M) | 0.12 (0.25 M) |
| D-Raffinose | | 12.2 (2.5 mM) | 13.6 (0.125 M) |
| Alpha-D-Melibiose | | 25 (10 mM) | 32.5 (0.25 M) |
| Amylose | | 0 (Saturated) | $6.07 \times 10^{-2}$ (Saturated) |
| α-Cellulose | | 0 | 0.03 (Saturated) |
| Starch (from corn) | | 0 | 0.003 (Saturated) |
| Starch (soluble) | | 0 | 0.018 (Saturated) |
| 4-Pyridylcarbinol | | 7.74 (100 mM) | 41.7 (0.5 mM) |

TABLE 4A-continued

Substrate specificity of the wild-type (Fusarium GAO) and mutant (RQW) GAOs.
Substrate concentration is indicated within parentheses.

| Substrate Name | Substrate Structure | Wild-Type Activity (U/mg) | Mutant Activity (U/mg) |
| --- | --- | --- | --- |
| Dihydroxylacetone | HOH$_2$C−C(=O)−CH$_2$OH | 41.7 (3 mM) | 52.2 (0.3 mM) |
| 2-Propanol | H$_3$C−CH(OH)−CH$_3$ | 2.09 × 10$^{-2}$ (0.5 M) | 2.98 (0.5 M) |
| 3-Buten-2-ol | H$_2$C=CH−CH(OH)−CH$_3$ | 3.52 × 10$^{-2}$ (0.5 M) | 3.52 (0.5 M) |
| 3,3-Dimethyl-2-Butanol | H$_2$C=CH−CH(OH)−CH$_3$ | 0 (Saturated) | 2.85 (Saturated) |
| 2-Octanol | CH$_3$(CH$_2$)$_5$CH$_2$OHCH$_3$ | 0 (Saturated) | 2.85 (Saturated) |

Figure 3:
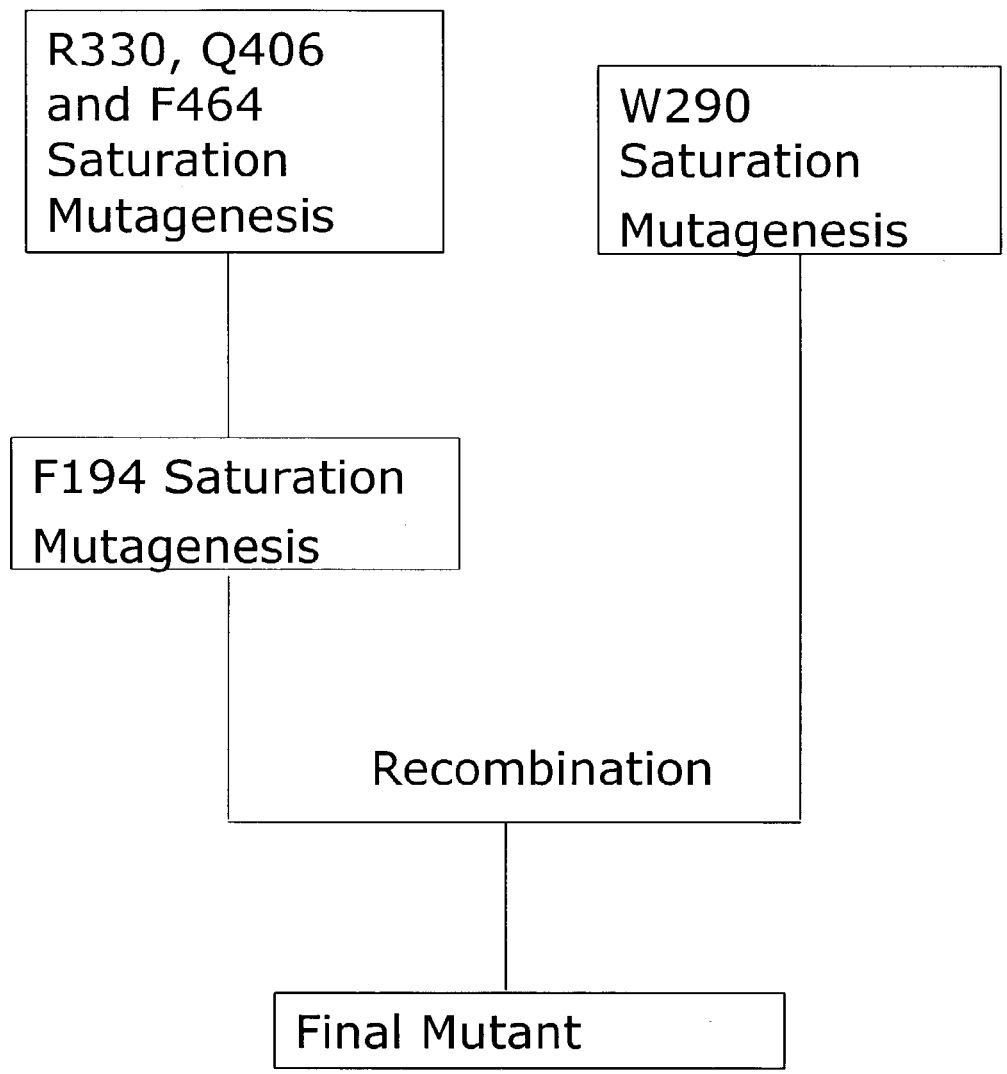
FIG. 3 shows an exemplary strategy for designing new and improved GAO mutants.

Oxidation of D-galactose by GAO generates a dialdehyde, whose tendency to form polymers complicates analysis. We therefore analyzed the product of M-RQW-catalyzed oxidation of methyl-β-D-gluco-pyranoside. FIG. 3 shows a thin-layer chromatogram of the reaction mixture and the silica-gel purified product. All product components were stained upon treatment of the TLC plates with Purpald reagent, a diagnostic for aldehydes. A single major product was found. Trace by-products are believed to be the dimer and α-β elimination product of the oxidation product (i.e., the sugar aldehyde) (Maradufu, A. and Perlin, A. S., (1974) Carbohyd. Res., 32, 127–136; Singh, S., et al. (1989) J. Org. Chem., 54, 2300–2307). The appearance of by-products after product purification indicates that they are generated non-enzymatically. By-products with the same retention times were observed in the reaction of native (Sigma) GAO with methyl-β-D-galacto-pyranoside.

$^{13}$C NMR spectroscopy revealed that the chemical shift of C6 in the substrate moved from 61 ppm to 89 ppm in the product. The identical shift was observed in the aldehyde product of methyl-β-D-galacto-pyranoside oxidation by wild-type GAO. $^1$H NMR spectra also showed formation of the aldehyde by appearance of a signal with chemical shift 5.25 ppm. No oxidation was detected at the other positions. Oxidation of D-glucose by mutant M-RQW is thus specific to the 6-OH group.

Activities of M-RQW and wild-type GAO towards various alcohols (Table 3B) show a substantially different substrate specificities for the mutant. The relative rates of reaction of native and mutant GAO towards different alcohols are shown in Table 3B. M-RQW oxidizes several substrates on which the native enzyme is inactive, including D-glucose and its derivatives as well as several aliphatic secondary alcohols.

TABLE 4B

Relative rates of reaction of native and mutant GAO.
Activities are reported relative to D-galactose (=100).
Wild-type enzyme is 1000 times more active on D-galactose
than the M-RQW mutant

| Substrate | Wild-Type GAO | Mutant M-RQW |
| --- | --- | --- |
| D-Galactose | 100 | 100 |
| D-Glucose | 0 | 4.8 |
| 2-Deoxy- D-glucose | 0 | 3.9 |
| Methyl-β-D-gluco-pyranoside | 0 | 3.3 |
| D-Mannose | 0 | 0.002 |
| β-D-Lactose | 48 | 18.7 |
| L-Galactose | 0 | 1.5 |
| Allyl alcohol | 0.3 | 2500 |
| D-Maltose | 0 | 0.45 |
| Amylose | 0 | 0.23 |
| 2-Pyridylcarbinol | 0.6 | 180000 |
| 3-Pyridylcarbinol | 5 | 35000 |
| 4-Pyridylcarbinol | 1.3 | 81000 |
| Dihydroxyacetone | 200 | 1600 |
| 2-Propanol | 0 | 5.7 |
| 3-Buten-2-ol | 0 | 6.9 |

Figure 4:
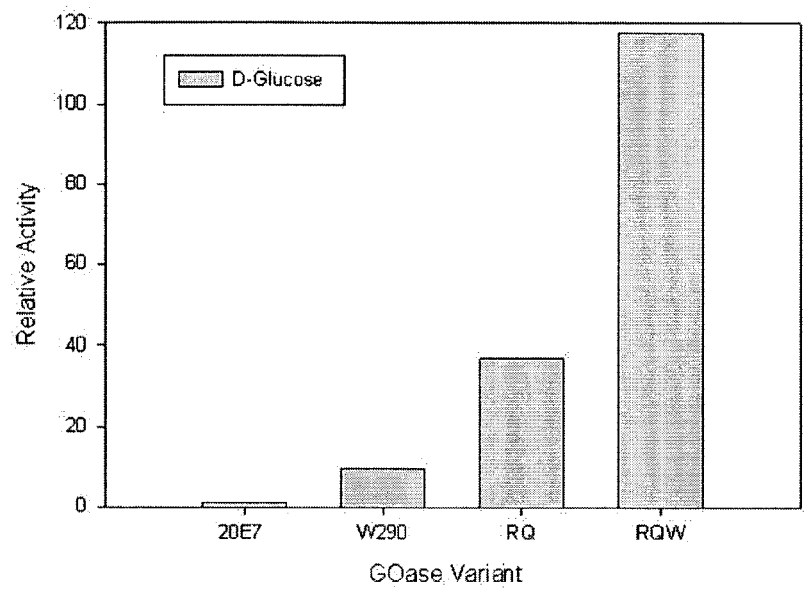
FIG. 4 shows the relative activities of selected GAO mutants for the novel substrate D-glucose and the "wild-type" substrate D-galactose.
Figure 4:
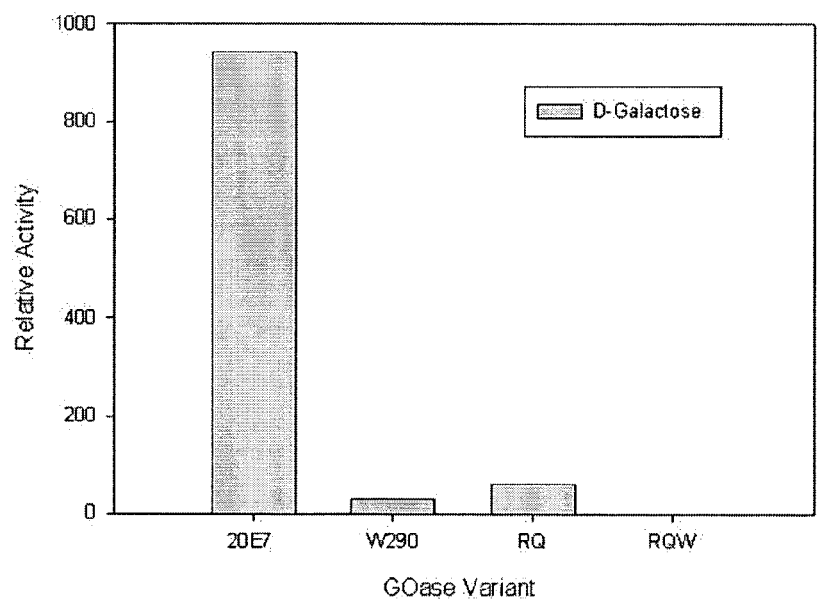
Figure 5:
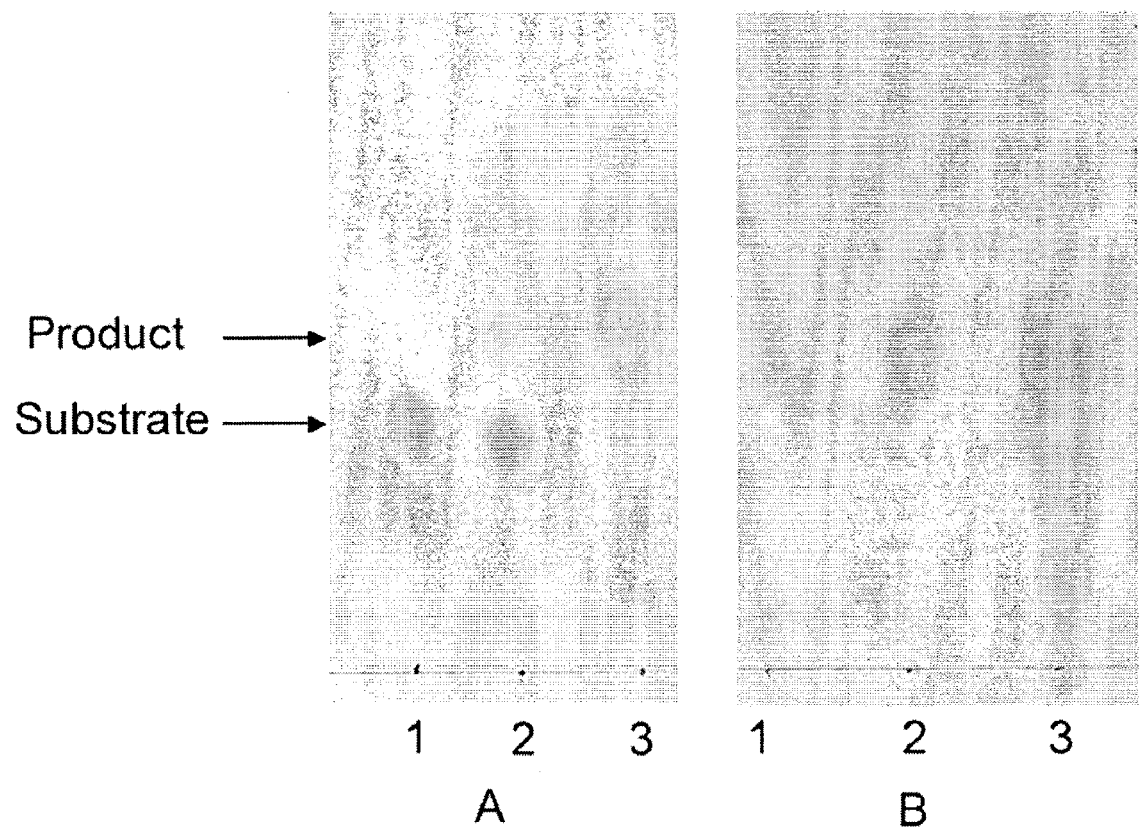
FIG. 5 shows a thin layer chromatogram (TLC) of a methyl-β-D-gluco-pyranoside oxidation reaction by the engineered GAO mutant RQW. TLC plates were stained using Bail's reagent (A) and Purpald reagent (B). Lane 1: substrate; lane 2: reaction mixture; lane 3: purified product.
Figure 6:
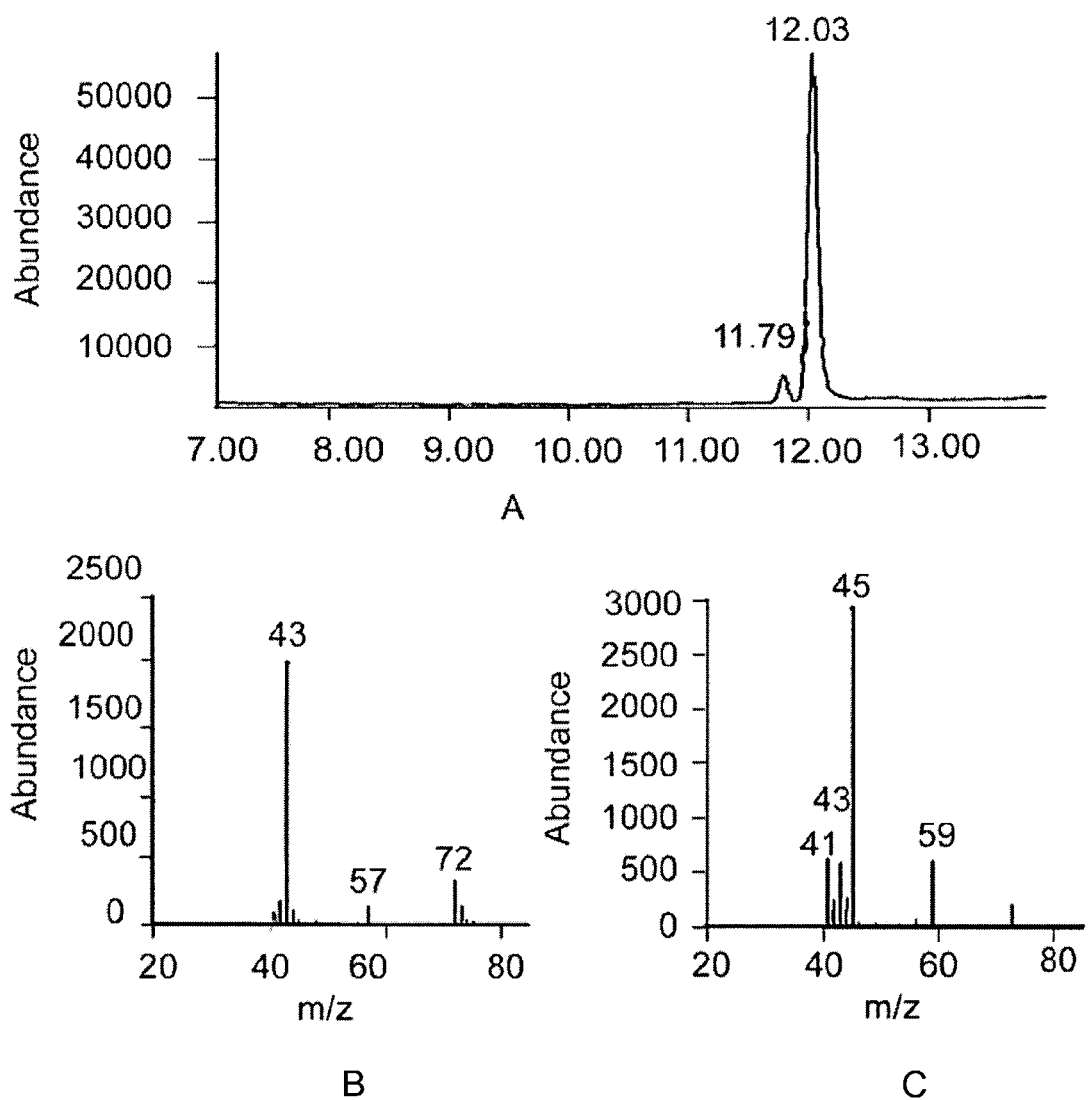
FIG. 6 shows a gas chromatography-mass spectrometry (GC-MS) analysis of a 2-butanol oxidation reaction by the mutant M-RQW. (A) GC spectrum of the reaction mixture. (B) and (C) MS spectra of the two components, 2-butanol and 2-butanone, in the reaction mixture.

The oxidation of secondary alcohols by GAO has not been reported previously. GC-MS analysis of the reaction mixture of M-RQW with 2-butanol showed the appearance of a new peak whose identity was confirmed as 2-butanone. (See FIGS. 4A–C). In FIG. 4, the component with the retention time 11.79 minutes is 2-butanone, and the component with the retention time 12.09 minutes is 2-butanol.

Various primary alcohols with a carbonyl or aromatic group in the $_c$-position, including 3-pyridylcarbinol and dihydroxyacetone, are also better substrates for the mutant than for the native enzyme. M-RQW is very efficient on some of these: on 2-pyridylcarbinol, for example, M-RQW has higher specific activity than the wild-type enzyme has on D-galactose. M-RQW is also more active than wild-type GAO towards dihydroxyacetone, the best substrate for wild-type GAO, mainly due to a more than 6-fold decrease in $K_m$ (2.7 mM vs. 17 mM for wild-type enzyme). Apparently, accessibility to the active site has been significantly augmented to create a more broadly specific oxidase, and this broad specificity has not necessarily undermined the enzyme's catalytic activity.

D-galactose is still a fairly good substrate for M-RQW, which is ~20 times more active on D-galactose than on D-glucose. M-RQW's activity towards D-mannose is more than 2000 times lower than its activity on the 2-epimer of D-mannose, D-glucose, demonstrating how important the configuration at C-2 is for D-glucose binding. 2-Deoxy-D-glucose is a good substrate compared to D-glucose.

Mutant M-RQW is, among other things, a glucose 6-oxidase with a regioselectivity that has not been reported in nature. Glucose 1-oxidase, glucose 2-oxidase (pyranose oxidose), glucose 2,3-dehydrogenase and galactose 6-oxidase (GAO), are all produced by fungi and presumably function to generate $H_2O_2$ to facilitate lignin degradation. There is evidence that *Pseudogluconobacter saccharoketogenes* produces an enzyme that oxidizes the hydroxylmethyl group of the terminal glucose residue of a cyclomaltooligosaccharide, to produce a carboxylic acid(Ishiguro, T. et al. (2001), Carbohydr. Res., 331, 423). It is not known why the oxidation of glucose at the 6-hydroxyl to make aldehydes is unknown in nature. Combinatorial mutagenesis of GAO, however, and screening for activity on glucose has generated an enzyme with a significant level of this activity (1.6 U/mg). In addition, the M-RQW enzyme can be further improved to make even better glucose 6-oxidase enzymes, for synthetic or other applications.

Example 2

Improving Glucose-6 Oxidase Activity of Mutant RQW

This Example describes the application of saturation mutagenesis of mutant RQW to identify an additional mutation having a beneficial effect on D-glucose activity. The experiment was conducted to further improve the useful and novel activity of glucose oxidation.

Briefly, saturation mutagenesis was performed on residue Tyr329 of mutant M-RQW. In the native galactose oxidase, residue Tyr329 is important for substrate binding (Wachter and Branchaud (1996) J Am Chem Soc 118, 2782–2789).

The QuikChange Multi Site-Directed Mutagenesis Kit (Stratagene, La Jolla, Calif.) was used to perform site-directed mutagenesis on the plasmid carrying the M-RQW gene. Vector pGAO-036 carrying the GOase gene is a derivative of pUC-18 vector with double lac promoters. The GOase gene with the triple mutation of RQW was ligated into this plasmid between restriction sites of HindIII and XbaI.

The primers used were:

```
G GCT GAC AAG CAA GGA TTG NN(G/C) AAG TCA GAC AAC CAC GCG and    (SEQ ID NO:13)

CGC GTG GTT GTC TGA CTT (G/C)NN CAA TCC TTG CTT GTC AGC C.      (SEQ ID NO:14)
```

The PCR conditions were as follows: 94° C. for 30 s, 18 cycles at 94° C. for 30 s, 55° C. for 1 min and 68° C. for 9 minutes 30 seconds. The PCR product was digested with Dpn1 enzyme, purified with a Qiagen PCR purification kit and transformed to BL21 (DE3) by electroporation. (The electroporator was set to 23 µF, 200 Ohms and 2.5 kV). 91 mutants in this saturation mutagenesis library were cultured in a 96-well plate and were screened for activity towards glucose. This library size would give all the 32 possible codons at a confidence level of around 95 percent.

Figure 7:
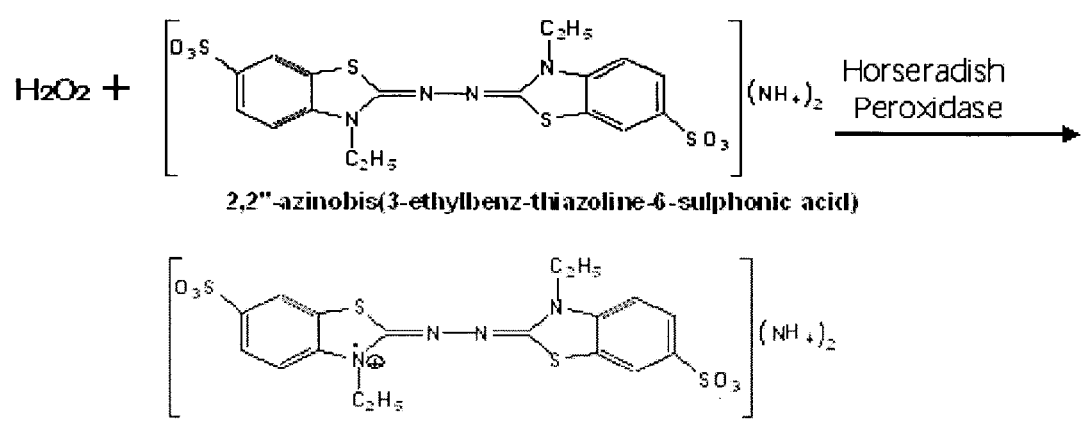
FIG. 7 shows the reaction scheme for horseradish peroxidase-catalyzed polymerization of ABTS in the presence of hydrogen peroxide. This reaction can be used for detecting glucose-6 oxidation activity in a high-throughput screening setting.

An ABTS-HRP system was used to assay the enzyme activity by measuring the formation of hydrogen peroxide (see above). As shown in FIG. 7, horseradish peroxidase catalyzes the polymerization of ABTS in the presence of hydrogen peroxide, and the green ABTS polymers can be monitored by the absorbance at 405 nm.

Aliquots of the 91 cell extracts were reacted with D-glucose and D-galactose at pH of 7.0, and the initial rate (for the galactose activity assay) and the endpoints (for the glucose activity assay) of the hydrogen peroxide formation was recorded by monitoring the HRP catalyzed oxidation of ABTS at 405 nm on a Thermomax microplate reader (Molecular Devices, Sunnyvale, Calif.).

Figure 8:
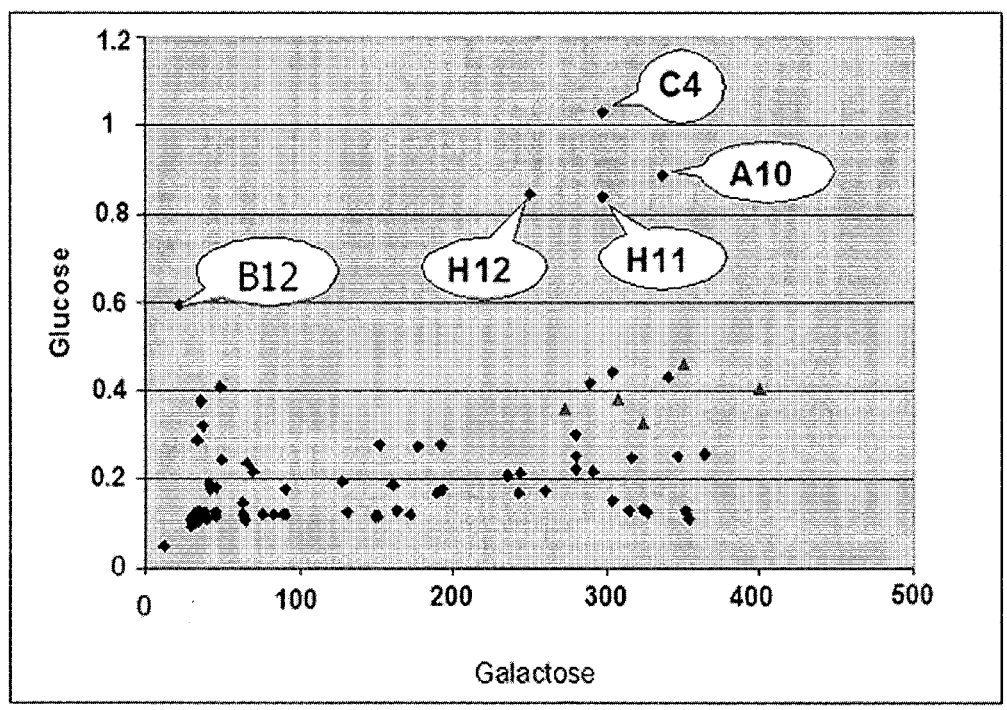
FIG. 8 shows the results of saturation mutagenesis of Tyr329 in mutant RQW. The y-axis represents activity on D-glucose, recorded as endpoints. The x-axis represents activity on D-galactose, recorded as initial rate. Dots represent clones in the saturation mutagenesis library. Triangles represent the activity of mutant RQW.

The five clones indicated above were cultured in larger scale (in 5 ml LB-ampicillin media) and the ABTS-HRP assay was performed again to confirm the increased activity. See FIG. 8. Mutants H11 and H12 showed higher activity on both glucose and galactose in each assay. Plasmids were recovered from these clones, and a region of about 600 bp around the saturation mutagenesis site was sequenced. The two mutants were found to have the same mutation at site 329: TAC->CGC, which leads to the amino acid substitution of Tyr329 by Arg.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application and in the appended bibliography, the disclosures of which are incorporated herein by reference in their entireties for all purposes.

BIBLIOGRAPHY

GAO Literature

Amaral, D., et al. (1966) Methods Enzymol. 9, 87–2.

Arts, S. J. H. F., Monbarg, E. J. M., et al. (1997), Synthesis, June 1997, 597–613; Kosman, D. J. (1984), in Lontie, R., Eds., Copper proteins and copper enzymes, Vol. 2., CRC Press, Boca Raton, Fla., 1–26.

Arts, S. J. H. F., et al. (1997), Synthesis, June 1997, 597–613

Avigad, G. (1985), Arch. Biochem. Biophys., 239(2), 531–537.

Avigad, G. (1978), Anal. Biochem., 86, 470–476.

Avigad, G., et al., (1962) J. Biol. Chem. 237, 2736–2743

Baron, A. J., et al. (1994) J. Biol. Chem. 269, 25095–25105

Hamilton, F. A., et al. (1978), J. Am. Chem. Soc., 100(6), 1899–1912.

Hamilton, G. A., et al. (1973), In King, T. E., et al. Eds., Oxidases and related redox enzyme, University Park Press, Baltimore, Md., 103–124.

Ito, N., et al.(1994) J. Mol. Biol. 238, 794–814

Ito, N., et al. (1991) Nature 350, 87–90

Kiba, N., et al. (1989), J. Chromatogr., 463, 183–187.

Klibanov, A. M., et al. (1982) Biochem. Biophys. Res. Commun. 108, 804–808

Koroleva, O. V., et al. (1983), Prikl. Biokhim. Mikrobiol., 19(5), 632–637.

Kosman, D. J. (1984), in Lontie, R., Eds., Copper proteins and copper enzymes. Vol. 2., CRC Press, Boca Raton, Fla., 1–26

Lis, M., and Kuramitsu, H. K. (1997), Antimicrob. Agents Chemother., 41(5), 999–1003.

Maradufu, A., et al. (1974), Carbohydr. Res. 32, 93–99.

Martin, B. D., et al. (1998), Biomaterials, 19(1–3), 69–76.

Mazur, A. W., and Hiler, G. D. (1997) J. Org. Chem. 62, 4471–4475

McPherson, M. J., et al. (1992), J. Biol. Chem., 267(12), 8146–8152.

McPherson, M. J., et al. (1993), Biochem. Soc. Transact., 21, 752–756.

Mendonca, M. H., and Zancan, G. T. (1987) Arch. Biochem. Biophys. 272, 507–514

Mendonca, M. H., and Zancan, G. T. (1988), Arch. Biochem. Biophys., 266(2), 427–434.

Reynolds, M. P., et al. (1997) J. Biol. Inorg. Chem. 2, 327–335

Root, R. L., et al. (1985) J. Am. Chem. Soc. 107, 2997–2999

Saysell, C. G., et al. (1997), JBIC, 2, 702–709.

Schlegel, R. A., et al. (1968), Carbohydr. Res., 7, 193–199

Tressel, P. (1980) Ph.D. Thesis, State University of New York, Buffalo.

Tressel, P., and Kosman, D. J. (1980), Anal. Biochem., 105, 150–153.

Tressel, P. S., and Kosman, D. J. (1989), Methods Enzymol., 89, 163–171.

Wachter, R. M., and Branchaud, B. L. (1996) J. Am. Chem. Soc. 118, 2782–2789

Whittaker, M. M., et al. (1998), Biochemistry, 37, 8426–8436.

General Literature

Adanyi, N., Szabo, E. E., and Varadi, M. (1999) European Food Research and Technology 209, 220–226.

Aisaka, K., and Terada, O. (1981), Agric. Biol. Chem., 45(10), 2311–2316.

Amaral, D., Bernstein, L., Morse, D. And Horecker, B. L. (1963) J. Biol. Chem., 238, 2281–2284.

Amaral, D., Kelly-Falcoz, F., and Horecker, B. L. (1966) Methods Enzymol. 9, 87–2.

Arkin, A. and Youvan, D. C. Proc. Natl. Acad. Sci. USA 89, 7811 (1992).

Arnold, F. H. Accounts Chem. Res. 31, 125 (1998).

Arts, S. J. H. F., Mombarg, E. J. M., van Bekkum, H., and Sheldon, R. A. (1997) Synthesis-Stuttgart 6, 597–610.

Arts, S. J. H. F., Monbarg, E. J. M., van Bekkum, H., and Sheldon, R. A. (1997) Synthesis, June, 1997, 597–613.

Avigad, G. (1978), Anal. Biochem., 86, 470–476.

Avigad, G., Amaral D., Asensio, C., and Horecker, B. L. (1962) J. Biol. Chem. 237, 2736–2743.

Avigad, G. (1985), Arch. Biochem. Biophys., 239(2), 531–537.

Baron, A. J., Stevens, C., Wilmot, C., Seneviratne, K. D., Blakeley, V., Dooley, D. M., Phillips, S. E. V., Knowles, P. F., and McPherson, M. J. (1994) J. Biol. Chem. 269, 25095–25105.

Beckman, R. A.; Mildvan, A. S.; Loeb, L. A. Biochemistry 24, 5810 (1994).

Better, M.; Chang, C. P.; Robinson, R. R.; Horwitz, A. H. Science 240, 1041 (1988).

Borman, C. D., Saysell, C. G., and Sykes, A. G. (1997) J. Biol. Inorg. Chem. 2, 480–487.

Calderhead, D. M., and Lienhard, G. E. (1988) J. Biol. Chem. 263, 12171–12174.

Caldwell, R. C.; Joyce, G. F. PCR Methods Applic. 2, 28 (1992).

Carbon, J.; Clarke, L.; Ilgen, C.; Ratzkin, B. In: Recombinant Molecules: Impact on Science and Society; Beers, R. F. J., Bassett, E. G., Eds; Raven Press: New York, pp 355–378 (1977).

Castelli, M. C. et al., Gene 142, 113 (1994).

Chen, K. & Arnold, F. H. (1993) Proc. Natl. Acad. Sci. USA, 90, 5618–5622

Cherry, J. R., Lamsa, M. H., Schneider, P., Vind, J., Svendson, A., Jones, A., & Pederson, A. H. (1999) Nat. Biotechnol., 17, 379–384

Cooper, J., Smith, W., Bacila, M., and Medina, H, (1959), J. Biol. Chem., 234–445.

Crameri, A.; Whiteborn, E. A.; Tate, E.; Stemmer, W. P. C. Nature Biotechnol. 14, 315 (1996).

Dahlhoff, W. V., Idelmann, P., and Koster, R., (1980) Angew. Chem. Int. Ed. Engl. 19, 546–547.

De Sutter, K.; Hostens, K.; Vandekerckhove, J.; Fiers, W. GENE 141, 163 (1994).

Delagrave et al. Bio/Technology 11, 1548 (1993)

Delagrave et al. Protein Engineering 6, 327 (1993).

Dunford, H. B. (1991) Peroxidases in Chemistry and Biology, Vol 2. pp. 1–24

Egorov, A. M.; Gazaryan, I. G.; Savelyev, S. V.; Fechina, V. A.; Veryovkin, A. N.; Kim, B. B. Ann. N. Y. Acad. Sci. 646, 35 (1991).

Fiedler, K. & Simons, K. (1995) Cell, 81, 309–312

Fitzgerald, M. M.; Churchill, M. J.; McRee, D. E.; Goodin, D. B. Biochemistry 33, 3807 (1994).

Gahmberg, C. G., and Tolvanen, M. (1994) Methods Enzymol. 230, 32–44.

Gajhede, M.; Schuller, D. J.; Henriksen, A.; Smith, A. T.; Poulos, T. L. Nature Struct. Biol. 4, 1032 (1997).

Gazaryan, I. G. (1994) LABPV Newsletters, 4, 8–15

Gietz, D., Schiestl, R. H., Willems, A., Woods, R. A., Yeast 11, 355 (1995).

Gillam, E. M., Guo, Z., Martin, M. V., Jenkins, C. M. & Guengerich, F. P. (1995) Arch. Biochem. Biophys., 319, 540–550.

Giver, L., Gershenson, A., Freskgard, P-O. & Arnold, F. H. (1998) Proc. Natl. Acad. Sci. USA, 95, 12809–12813

Glover, D. M. (ed.), 1985, DNA Cloning: A Practical Approach, MRL Press, Ltd., Oxford, U.K. Vol. 1, II.

Goldman, E. R. and Youvan D. C. Bio/Technology 10,1557 (1992).

Goodin, D. B.; Davidson, M. G.; Roe, J. A.; Mauk, A. G.; Smith, M. Biochemistry 30, 4953 (1991)

Goshorn, S. C.; Svensson, H. R.; Kerr, D. E.; Somerville, J. E.; Senter, P. D.; Fell, H. P. Cancer Res. 53, 2123 (1993).

Gramm, H. et al., Proc. Natl. Acad. Sci. USA 89, 3576 (1992).

Guengerich, F. P., Martin, M. V., Guo, Z. & Chun, Y. J. (1996) Meth. Enzymol., 272, 35–44.

Gussow, D. & Clackson, T. (1989) Nucleic Acids Res., 17, 4000–4000.
Hamilton, G. A., de Jersey, J., and Adolf, P. K. (1973). In King, T. E., et al. ds., Oxidases and related redox enzyme, University Park Press, Baltimore, Md., 103–124.
Hamilton, F. A., Adolf, P. K., de Jersey, J., DuBois, G. C., Dyrkacz, G. R., and Libby, D. (1978). J. Am. Chem. Soc., 100(6), 1899–1912.
Helenius, A. (1994) Mol. Biol. Cell., 5, 253–265
Hermes, J. D. et al., Proc. Natl. Acad. Sci. USA 87, 696 (1990).
Hopps, H. B., (2000) Aldrichimica Acta, 33, 28.
Howitz, M. S. and Loeb, L. A. (1986). Proc. Natl. Acad. Sci. USA. 83, 7406–7409.
Ishiguro, T., Fuse, T. Oka, M., Kurasawa, T., Nakamichi, M., Yasumura, Y., Tsuda, M., Yamaguchi, T., Nogami, I., (2001), Carbohydr. Res., 331, 423.
Ito, N., Knowles, P. F., and Phillips, S. E. V. (1995) Methods Enzymol. 258, 235–262.
Ito, N., Phillips, S. E. V., Stevens, C., Ogel, Z. B., McPherson, M. J., Keen, J. N., Yadav, K. D. S., and Knowles, P. F. (1991) Nature 350, 87–90.
Ito, N., Phillips, S. E. V., Yadav, K. D. S., and Knowles, P. F. (1994) J. Mol. Biol. 238, 794–814.
Joo, H., Lin, Z. & Arnold, F. H. (1999) Nature , 399, 670–673.
Joo, H. Arisawa, A., Lin, Z. & Arnold, F. H. (1999) Chem. Biol., 6, 669–706.
Khosla, C., Curtis, J E, Demodena, J., Rinas, U. & Bailey, J E (1990) Bio/Technology, 8, 849–853.
Kiba, N., Shitara, K., and Furusawa, M. (1989), J. Chromatogr., 463, 183–187.
Klibanov, A. M., Alberti, B. N., and Marletta, M. A. (1982) Biochem. Biophys. Res. Commun. 108, 804–808.
Koroleva, O. V., Rabinovich, M. L., Buglova, T. T., and Yaropolov, A. I. (1983), Prikl. Biokhim. Mikrobiol., 19(5), 632–637.
Kosman, D. J. (1984). In: Lontie, R., Eds., Copper proteins and copper enzymes. Vol. 2., CRC Press, Boca Raton, Fla., 1–26.
Koster, R., Idelmann, P., and Dahlhoff, W. V. (1982) Synthesis, 650–652.
Kyte J., In: Structure in Protein Chemistry, Garland Publishing Inc., New York & London, 1995, pp. 243–278.
Lei, S. P.; Lin, H. C.; Wang, S. S.; Callaway, J.; Wilcox, G. J. Bacteriol. 169, 4379 (1987).
Leung, D. W. et al. (1989), Technique 1, 11–15.
Lis, M., and Kuramitsu, H. K. (1997), Antimicrob. Agents Chemother., 41(5), 999–1003.
Liu, X. C., and Dordick, J. S. (1999) J. Am. Chem. Soc. 121, 466–467.
Mannino, S., Cosio, M. S., and Buratti, S. (1999) Italian Journal of Food Science 11, 57–65.
Maradufu, A. And Perlin, A. S., (1974) Carbohyd. Res., 32, 127–136.
Maradufu, A., Cree, G. M., and Perlin, A. S. (1971) Canad. J. Chem. 49, 3429–3436.
Maradufu, A., et al. (1974), Carbohydr. Res. 32, 93–99.
Marrs, B. L. in IBC's Fifth Annual World Congress on Enzyme Technologies (2000) Las Vegas, Nev.
Martin, I. G., Macias, E. M., Sanchez, J. S., and Rivera, B. G. (1998) Food Chemistry 61, 281–286.
Martin, B. D., Linhardt, R. J., and Dordick, J. S. (1998), Biomaterials, 19(1–3), 69–76.
Mazur, A. In: Enzymes in Carbohydrate Synthesis (1991) Bednarski, M. D. and Simon, E. S. Eds, pp. 99–110.
Mazur, A. W., and Hiler, G. D. (1997) J. Org. Chem. 62, 4471–4475.
McPherson, M. J., Ogel, Z. B., Stevens, C., Yadav, K. D. S., Keen, J. N., and Knowles, P. F. (1992), J. Biol. Chem., 267(12), 8146–8152.
McPherson, M. J., Stevens, C., Baron, A. J., Ogel, Z. B., Sneviratne, K., Wilmot, C., Ito, N., Brocklebank, I., Phillips, S. E. V., and Knowles, P. F. (1993), Biochem. Soc. Transact., 21, 752–756.
Mendonca, M. H., and Zancan, G. T. (1987) Arch. Biochem. Biophys. 272, 507–514.
Mendonca, M. H., and Zancan, G. T. (1988), Arch. Biochem. Biophys., 266(2), 427–434.
Miele, R. G., Prorok, M., Costa V. A. & Castellino F. J. (1999) J.Biol.Chem., 274, 7769–7776
Miyazaki, K., Wintrode, P. L., Grayling, R. A., Rubingh, D. N. & Arnold, F. H. (2000) J.Mol.Biol. in press.
Miyazaki, K. and Arnold, F. H. (1999) J. Mol. Evol. 49, 716–720
Moore, J. C.; Arnold, F. H. Nature Biotechnol. 14, 458 (1996).
Nagayama, Y., Namba, H., Yokoyama, N., Yamashita, S. & Niwa, M. (1998) J. Biol. Chem., 273, 33423–33428
Oliphant, A. R. et al., Gene 44, 177 (1986).
Ortlepp, S. A.; Pollard-Knight, D.; Chiswell, D. J. J. Biotechnol. 11, 353 (1989).
Ostermeier, M.; Desutter, K.; Georgiou, G. Eukaryotic J. Biol. Chem. 271, 10616 (1996).
Rathore, D.; Nayak, S. K.: Batra, J. K. FEBS Lett. 392, 259 (1996).
Reynolds, M. P., Baron, A. J., Wilmot, C. M., Vinecombe, E., Stevens, C., Phillips, S. E. V., Knowles, P. F., and McPherson, M. J. (1997) J. Biol. Inorg. Chem. 2, 327–335.
Rodriguez-Lopez, J. N., Smith, A. T., and Thorneley, R. N. F. (1995) J.Biol.Chem., 271, 4023–4030
Romanos, M. A., Scorer, C. A. & Clare J. J. (1992) Yeast , 8, 423–488
Root, R. L., Durrwachter, J. R., and Wong, C. H., (1985) J. Am. Chem. Soc. 107, 2997–2999.
Said, I. T., Shamsuddin, A. M., Sherief, M. A., Taleb, S. G., Aref, W. F., and Kumar, D.(1999) Histol. Histopathol. 14, 351–357.
Savenkova, M. I.; Kuo, J. M.; Ortiz de Montellano, P. R. Biochemistry 37, 10828 (1998).
Saysell, C. G., Barna, T., Borman, C. D., Baron, A. J., McPherson, M. J., and Sykes, A. G. (1997), JBIC, 2, 702–709.
Schatz, P. J. et al., Annu. Rev. Genet. 24, 215–248 (1990).
Schlegel, R. A., Gerbeck, C. M., and Montgomery, R. (1968), Carbohydr. Res., 7, 193–199.
Shafikhani, S.; Siegel, R. A.; Ferrari, E.; Schellenberger, V. Biotechniques 23, 304 (1997).
Singh, S., Nambiar, S., Porter, R. A., Sander, T. L. and Taylor, K. G., (1989) J. Org. Chem., 54, 2300–2307.
Sirotkin, K. J. Theor. Biol. 123, 261 (1986).
Smith, A. T. et al. J. Biol. Chem. 265, 13335–13343 (1990).
Smith, A. T., & Veitch, N. C. (1998) Curr.Opin.Chem.Biol., 2, 269–278
Stemmer, W. P. C. Proc. Natl. Acad. Sci. USA 91, 10747–51 (1994).
Stemmer, W. P. C. et al., Biotechniques 14, 256 (1992).
Studier, F. W.; Rosenberg, A. H.; Dunn, J. J.; Dubendorff, J. W. Meth. Enzymol. 185, 60 (1990).
Sun, L., Petrounia, I. P., and Arnold, F. H. (2001) Protein Eng. 14, 699–704.

Szabo, E. E., Adanyi, N., and Varadi, M. (1996) Biosensors & Bioelectronics 11, 1051–1058.
Tams, J. W.; Welinder, K. G. FEBS Lett. 421, 234 (1998).
Tkac, J., Gemeiner, P., and Sturdik, E. (1999) Biotechnology Techniques 13, 931–936.
Tressel, P. (1980) Ph.D. Thesis, State University of New York, Buffalo.
Tressel, P. S., and Kosman, D. J. (1989), Methods Enzymol., 89, 163–171.
Tressel, P., and Kosman, D. J. (1980), Anal. Biochem., 105, 150–153.
Vega, F. A., Nunez, C. G., Weigel, B., Hitzmann, B., and Ricci, J. C. D. (1998) Anal. Chim. Acta 373, 57–62.
Vrbova, E., Peckova, J., and Marek, M. (1992) Collection of Czechoslovak Chemical Communications 57, 2287–2294.
Wachter, R. M., and Branchaud, B. L. (1996) J. Am. Chem. Soc. 118, 2782–2789.
Welinder, K. G., Eur J. Biochem 96, 483–502 (1979).
Whitaker, M. W., and Whitaker, J. W. (1988) J. Biol. Chem. 263, 6074–6080.
Whittaker, M. M., Ballou, D. P., and Whittaker, J. W. (1998), Biochemistry, 37, 8426–8436.
Yang, G. Y., and Shamsuddin, A. M. (1996) Histol. Histopathol. 11, 801–806.
Yano, T., Oue, S. & Kagamiyama, H. (1998) Proc. Natl. Acad. Sci. USA, 95, 5511–5515
Zhao, H. M.; Arnold, F. H. Nucleic Acids Res. 25, 1307 (1997).
Zhao, H. M. & Arnold, F. H. (1999) Protein Eng. 12, 47–53

Patent Literature

WO 01/88110
WO 98/42832
WO 95/22625
WO 97/20078
WO 01/62938
U.S. Pat. No. 5,605,793
U.S. Pat. No. 5,830,721
U.S. Pat. No. 5,741,691
U.S. Pat. No. 5,811,238

What is claimed is:

1. A method of producing a glucose-6 oxidase comprising the steps of:
   (a) constructing a library of variants of a parent galactose oxidase (GAO), wherein the parent galactose oxidase has the amino acid sequence of SEQ ID NO:2, where said variant consists of an amino acid substitution at residue Q406 of SEQ ID NO:2 and one or two additional amino acid substitutions; and
   (b) selecting any galactose oxidase variants having increased glucose-6 oxidation activity as compared to the parent galactose oxidase, wherein said one or two additional amino acid substitutions are positioned at residues no more that 15 Å from a metal ion in the catalytic center of the parent galactose oxidase, based on 3-dimensinal structure of the amino acid sequence of SEQ ID NO:2, and wherein said one or two additional amino acid substitutions are at residues selected from the group consisting of S10, M70, P136, I169, V170, P171, A172, A173, A174, M185, W186, S187, S188, Y189, R190, N191, D192, A193, F194, G195, G196 S197, I201, T202, L203, H224, D225, M226, F227, C228, P229, G230, I231, V241, T242, G243, G244, N245, D264, A247, R270, G271, Y272, Q273, S274, S275, C287, G288, W290, S291, G292, G293, V294, K297, D324, Q326, G327, L328, Y329, R330, S331, D332, N333, H334, A335, W336, P350, A381, M382, C383, G384, N385, S402, D404, Y405, T440, F441, H442, T443, G457, R460, G461, I462, P463, F464, E465, D466, V492, R493, V494, Y495, H496, S497, I498, S499, G510, G511; G512, G513, L514, C515, G516, D517, C518, T520, N521, H522, N535, T578, A579, T580, H581, T582, V583, and A584 of SEQ ID NO:2.

2. The method of claim 1, wherein the library is produced by saturation mutagenesis.

3. The method of claim 1, wherein said one or two additional amino acid substitutions are at amino acid residues positioned no more than 10 Å from the metal ion.

4. The method of claim 1, wherein said one or two additional amino acid substitutions are at amino acid residues positioned no more than 7 Å from the metal ion.

5. The method of claim 1, wherein said one additional amino acid substitution is at residue R330, F464, W290, or Y329.

6. The method of claim 1, comprising selecting any variant having at least 10 times the glucose-6 oxidation activity of the parent galactose oxidase.

7. The method of claim 1, comprising selecting any variant having at least 100 times the glucose-6 oxidation activity of the parent galactose oxidase.

8. The method of claim 1, wherein the amino acid substitutions are selected from the group consisting of R330K, Q406S, Q406T, W290F, Y329R, V494A, S10P, M70V, G195E, and N535D.

* * * * *

SEQUENCE LISTING

```
<160> NUMBER OF SEQ ID NOS: 14

<210> SEQ ID NO 1
<211> LENGTH: 1917
<212> TYPE: DNA
<213> ORGANISM: Hypomyces rosellus

<400> SEQUENCE: 1
gcctcagcac ctatcggaag cgccatttct cgcaacaact gggccgtcac ttgcgacagt      60
gcacagtcgg gaaatgaatg caacaaggcc attgatggca acaaggatac cttttggcac     120
acattctatg gcgccaacgg ggatccaaag cccccctcaca catacacgat tgacatgaag    180
acaactcaga acgtcaacgg cttgtctatg ctgcctcgac aggatggtaa ccaaaacggc     240
tggatcggtc gccatgaggt ttatctaagc tcagatggca caaactgggg cagccctgtt     300
gcgtcaggta gttggttcgc cgactctact acaaaatact ccaactttga aactcgccct     360
gctcgctatg ttcgtcttgt cgctatcact gaagcgaatg gccagccttg gactagcatt     420
gcagagatca acgtcttcca agctagttct tacacagccc cccagcctgg tcttggacgc     480
tggggtccga ctattgactt accgattgtt cctgcggctg cagcaattga accgacatcg     540
ggacgagtcc ttatgtggtc ttcatatcgc aatgatgcat ttggaggatc ccctggtggt     600
atcactttga cgtcttcctg ggatccatcc actggtattg tttccgaccg cactgtgaca     660
gtcaccaagc atgatatgtt ctgccctggt atctccatgg atggtaacgg tcagatcgta     720
gtcacaggtg gcaacgatgc caagaagacc agtttgtatg attcatctag cgatagctgg     780
atcccgggac ctgacatgca agtggctcgt gggtatcagt catcagctac catgtcagac     840
ggtcgtgttt ttaccattgg aggctcctgg agcggtggcg tatttgagaa gaatggcgaa     900
gtctatagcc catcttcaaa gacatggacg tccctaccca atgccaaggt caacccaatg     960
ttgacggctg acaagcaagg attgtaccgt tcagacaacc acgcgtggct ctttggatgg    1020
aagaagggtt cggtgttcca agcgggacct agcacagcca tgaactggta ctataccagt    1080
ggaagtggtg atgtgaagtc agccggaaaa cgccagtcta accgtggtgt agcccctgat    1140
gccatgtgcg gaaacgctgt catgtacgac gccgttaaag gaaagatcct gacctttggc    1200
```

-continued

```
ggctccccag attatcaaga ctctgacgcc acaaccaacg cccacatcat caccctcggt    1260
gaacccggaa catctcccaa cactgtctt gctagcaatg ggttgtactt tgcccgaacg    1320
tttcacacct ctgttgttct tccagacgga agcacgttta ttacaggagg ccaacgacgt    1380
ggaattccgt tcgaggattc aacccctgta tttacacctg agatctacgt ccctgaacaa    1440
gacactttct acaagcagaa ccccaactcc attgttcgcg tctaccatag catttccctt    1500
ttgttacctg atggcagggt atttaacggt ggtggtggtc tttgtggcga ttgtaccacg    1560
aatcatttcg acgcgcaaat ctttacgcca aactatcttt acaatagcaa cggcaatctc    1620
gcgacacgtc ccaagattac cagaacctct acacagagcg tcaaggtcgg tgcagaatt    1680 acaatctcga cggattcttc gattagcaag gcgtcgttga ttcgctatgg tacagcgaca    1740
cacacggtta atactgacca gcgccgcatt ccctgactc tgacaaacaa tggaggaaat    1800
agctattctt tccaagttcc tagcgactct ggtgttgctt tgcctggcta ctggatgttg    1860
ttcgtgatga actcggccgg tgttcctagt gtggcttcga cgattcgcgt tactcag      1917
```

<210> SEQ ID NO 2
<211> LENGTH: 639
<212> TYPE: PRT
<213> ORGANISM: Hypomyces rosellus

<400> SEQUENCE: 2

```
Ala Ser Ala Pro Ile Gly Ser Ala Ile Ser Arg Asn Asn Trp Ala Val
1               5                   10                  15

Thr Cys Asp Ser Ala Gln Ser Gly Asn Glu Cys Asn Lys Ala Ile Asp
                20                  25                  30

Gly Asn Lys Asp Thr Phe Trp His Thr Phe Tyr Gly Ala Asn Gly Asp
            35                  40                  45

Pro Lys Pro Pro His Thr Tyr Thr Ile Asp Met Lys Thr Thr Gln Asn
        50                  55                  60

Val Asn Gly Leu Ser Met Leu Pro Arg Gln Gly Asn Gln Asn Gly
65                  70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
        115                 120                 125

Ile Thr Glu Ala Asn Gly Gln Pro Trp Thr Ser Ile Ala Glu Ile Asn
    130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ile
                165                 170                 175

Glu Pro Thr Ser Gly Arg Val Leu Met Trp Ser Ser Tyr Arg Asn Asp
            180                 185                 190

Ala Phe Gly Gly Ser Pro Gly Gly Ile Thr Leu Thr Ser Ser Trp Asp
        195                 200                 205

Pro Ser Thr Gly Ile Val Ser Asp Arg Thr Val Thr Val Thr Lys His
    210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255
```

```
Ser Asp Ser Trp Ile Pro Gly Pro Asp Met Gln Val Ala Arg Gly Tyr
            260                 265                 270

Gln Ser Ser Ala Thr Met Ser Asp Gly Arg Val Phe Thr Ile Gly Gly
            275                 280                 285

Ser Trp Ser Gly Gly Val Phe Glu Lys Asn Gly Glu Val Tyr Ser Pro
        290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Thr
            340                 345                 350

Ala Met Asn Trp Tyr Tyr Thr Gly Ser Gly Asp Val Lys Ser Ala
            355                 360                 365

Gly Lys Arg Gln Ser Asn Arg Gly Val Ala Pro Asp Ala Met Cys Gly
        370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Asn Ala His Ile
                405                 410                 415

Ile Thr Leu Gly Glu Pro Gly Thr Ser Pro Asn Thr Val Phe Ala Ser
            420                 425                 430

Asn Gly Leu Tyr Phe Ala Arg Thr Phe His Thr Ser Val Val Leu Pro
        435                 440                 445

Asp Gly Ser Thr Phe Ile Thr Gly Gly Gln Arg Arg Gly Ile Pro Phe
    450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Val Tyr His
                485                 490                 495

Ser Ile Ser Leu Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
        515                 520                 525

Thr Pro Asn Tyr Leu Tyr Asn Ser Asn Gly Asn Leu Ala Thr Arg Pro
    530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
        595                 600                 605

Asp Ser Gly Val Ala Leu Pro Gly Tyr Trp Met Leu Phe Val Met Asn
    610                 615                 620

Ser Ala Gly Val Pro Ser Val Ala Ser Thr Ile Arg Val Thr Gln
625                 630                 635

<210> SEQ ID NO 3
<211> LENGTH: 42
<212> TYPE: DNA
<213> ORGANISM: Artificial Sequence
<220> FEATURE:
```

```
<223> OTHER INFORMATION: PCR primer
<220> FEATURE:
<221> NAME/KEY: misc_feature
<222> LOCATION: (22)..(23)
<223> OTHER INFORMATION: where n may be a or g or c or t
<220> FEATURE:
<221> NAME/KEY: misc_feature
<222> LOCATION: (24)..(24)
<223> OTHER INFORMATION: where n may be g or c

<400> SEQUENCE: 3
gctgacaagc aaggattgta cnnntcagac aaccacgcgt gg                    42

<210> SEQ ID NO 4
<211> LENGTH: 42
<212> TYPE: DNA
<213> ORGANISM: Artificial Sequence
<220> FEATURE:
<223> OTHER INFORMATION: PCR primer for Lib-R
<220> FEATURE:
<221> NAME/KEY: misc_feature
<222> LOCATION: (19)..(19)
<223> OTHER INFORMATION: where n may be g or c
<220> FEATURE:
<221> NAME/KEY: misc_feature
<222> LOCATION: (20)..(21)
<223> OTHER INFORMATION: where n may be a or g or c or t

<400> SEQUENCE: 4
ccacgcgtgg ttgtctgann ngtacaatcc ttgcttgtca gc                    42

<210> SEQ ID NO 5
<211> LENGTH: 36
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (19)..(20)
<223> OTHER INFORMATION: where n may be a or g or c or t
<220> FEATURE:
<221> NAME/KEY: misc_feature
<222> LOCATION: (21)..(21)
<223> OTHER INFORMATION: where n may be g or c

<400> SEQUENCE: 5
ggccaacgac gtattccgnn ngaggattca accccg                           36

<210> SEQ ID NO 6
<211> LENGTH: 39
<212> TYPE: DNA
<213> ORGANISM: Artificial Sequence
<220> FEATURE:
<223> OTHER INFORMATION: PCR primer for Lib-RF
<220> FEATURE:
<221> NAME/KEY: misc_feature
<222> LOCATION: (16)..(16)
<223> OTHER INFORMATION: where n may be g or c
<220> FEATURE:
<221> NAME/KEY: misc_feature
<222> LOCATION: (17)..(18)
<223> OTHER INFORMATION: where n may be a or g or c or t

<400> SEQUENCE: 6
cggggttgaa tcctcnnncg gaattccacg tcgttggcc                        39

<210> SEQ ID NO 7
<211> LENGTH: 39
<212> TYPE: DNA
<213> ORGANISM: Artificial Sequence
```

```
<220> FEATURE:
<223> OTHER INFORMATION: PCR primer
<220> FEATURE:
<221> NAME/KEY: misc_feature
<222> LOCATION: (19)..(19)
<223> OTHER INFORMATION: where n may be g or c
<220> FEATURE:
<221> NAME/KEY: misc_feature
<222> LOCATION: (20)..(21)
<223> OTHER INFORMATION: where n may be a or g or c or t

<400> SEQUENCE: 7
ggttgtggcg tcagagtcnn nataatctgg ggaggcggc                    39

<210> SEQ ID NO 8
<211> LENGTH: 39
<212> TYPE: DNA
<213> ORGANISM: Artificial Sequence
<220> FEATURE:
<223> OTHER INFORMATION: PCR primer for Lib-RFQ
<220> FEATURE:
<221> NAME/KEY: misc_feature
<222> LOCATION: (19)..(20)
<223> OTHER INFORMATION: where n may be a or g or c or t
<220> FEATURE:
<221> NAME/KEY: misc_feature
<222> LOCATION: (21)..(21)
<223> OTHER INFORMATION: where n may be g or c

<400> SEQUENCE: 8
gccgcctccc cagattatnn ngactctgac gccacaacc                    39

<210> SEQ ID NO 9
<211> LENGTH: 45
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (26)..(27)
<223> OTHER INFORMATION: where n may be a or g or c or t
<220> FEATURE:
<221> NAME/KEY: misc_feature
<222> LOCATION: (28)..(28)
<223> OTHER INFORMATION: where n may be g or c

<400> SEQUENCE: 9
gcggtcttca tatcgcaatg atgcannnga aggatcccct ggtgg             45

<210> SEQ ID NO 10
<211> LENGTH: 45
<212> TYPE: DNA
<213> ORGANISM: Artificial Sequence
<220> FEATURE:
<223> OTHER INFORMATION: PCR primer for Lib-RFQF
<220> FEATURE:
<221> NAME/KEY: misc_feature
<222> LOCATION: (18)..(18)
<223> OTHER INFORMATION: where n may be g or c
<220> FEATURE:
<221> NAME/KEY: misc_feature
<222> LOCATION: (19)..(20)
<223> OTHER INFORMATION: where n may be a or g or c or t

<400> SEQUENCE: 10
caaccagggg atccttcnnn tgcatcattg cgatatgaag accac             45

<210> SEQ ID NO 11
<211> LENGTH: 45
<212> TYPE: DNA
```

```
<213> ORGANISM: Artificial Sequence
<220> FEATURE:
<223> OTHER INFORMATION: PCR primer
<220> FEATURE:
<221> NAME/KEY: misc_feature
<222> LOCATION: (15)..(16)
<223> OTHER INFORMATION: where n may be a or g or c or t
<220> FEATURE:
<221> NAME/KEY: misc_feature
<222> LOCATION: (17)..(17)
<223> OTHER INFORMATION: where n may be g or c

<400> SEQUENCE: 11
ccattggagg ctccnnnagc ggtggcgtat ttgagaagaa tggcg          45

<210> SEQ ID NO 12
<211> LENGTH: 45
<212> TYPE: DNA
<213> ORGANISM: Artificial Sequence
<220> FEATURE:
<223> OTHER INFORMATION: PCR primer for Lib-W
<220> FEATURE:
<221> NAME/KEY: misc_feature
<222> LOCATION: (29)..(29)
<223> OTHER INFORMATION: where n may be g or c
<220> FEATURE:
<221> NAME/KEY: misc_feature
<222> LOCATION: (30)..(31)
<223> OTHER INFORMATION: where n may be a or g or c or t

<400> SEQUENCE: 12
cgccattctt ctcaaatacg ccaccgctnn nggagcctcc aatgg          45

<210> SEQ ID NO 13
<211> LENGTH: 40
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (20)..(21)
<223> OTHER INFORMATION: where n may be a or g or c or t
<220> FEATURE:
<221> NAME/KEY: misc_feature
<222> LOCATION: (22)..(22)
<223> OTHER INFORMATION: where n may be g or c

<400> SEQUENCE: 13
ggctgacaag caaggattgn nnaagtcaga caaccacgcg               40

<210> SEQ ID NO 14
<211> LENGTH: 40
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (19)..(19)
<223> OTHER INFORMATION: where n may be g or c
<220> FEATURE:
<221> NAME/KEY: misc_feature
<222> LOCATION: (20)..(21)
<223> OTHER INFORMATION: where n may be a or g or c or t

<400> SEQUENCE: 14
cgcgtggttg tctgacttnn ncaatccttg cttgtcagcc               40
```